(12) United States Patent
Li et al.

(10) Patent No.: US 10,583,388 B2
(45) Date of Patent: Mar. 10, 2020

(54) AMINO ACIDS REACT WITH CARBON DIOXIDE (CO2) AND FORM NANOFIBERS AND NANOFLOWERS

(71) Applicant: West Virginia University, Morgantown, WV (US)

(72) Inventors: Bingyun Li, Morgantown, WV (US); Xianfeng Wang, Morgantown, WV (US); David Hopkinson, Morgantown, WV (US); James Hoffman, South Park, PA (US); Adefemi Egbebi, Bethel Park, PA (US); Kevin P. Resnik, White Oak, PA (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 15/609,373

(22) Filed: May 31, 2017

(65) Prior Publication Data

US 2017/0348631 A1    Dec. 7, 2017

Related U.S. Application Data

(60) Provisional application No. 62/345,282, filed on Jun. 3, 2016.

(51) Int. Cl.
*B01D 53/14* (2006.01)
*C01D 7/38* (2006.01)
(Continued)

(52) U.S. Cl.
CPC ..... *B01D 53/1493* (2013.01); *B01D 53/1475* (2013.01); *B01D 53/62* (2013.01);
(Continued)

(58) Field of Classification Search
None
See application file for complete search history.

(56) References Cited

U.S. PATENT DOCUMENTS 3,042,483 A  * 7/1962 Wolfram ............... B01D 47/00
                                            423/437.1
7,759,285 B2 * 7/2010 Shim .................. B01D 53/1475
                                            423/226
(Continued)

FOREIGN PATENT DOCUMENTS

EP           2205341 B1    2/2012

OTHER PUBLICATIONS

Yang, S., et al., A partially interpenetrated metal-organic framework for selective hysteretic sorption of carbon dioxide, 2012, Nature Materials, 710, vol. 11, Macmillan Publishers Limited.
(Continued)

*Primary Examiner* — Joseph D Anthony
(74) *Attorney, Agent, or Firm* — Buchanan Ingersoll & Rooney PC

(57) ABSTRACT

A method for capturing $CO_2$ comprising dissolving at least one pure amino acid (AA) in water without the use of a catalyst for establishing protonation of an amino group of the amino acid, adding at least one base solution to the amino acid and water solution to deprotonate the protonated amino group of the amino acid and forming an amino acid-XOH—$H_2O$ wherein X is sodium or potassium, and subjecting $CO_2$ to the amino acid-XOH—$H_2O$ to form new nanomaterials is provided. A regenerable nanofiber is disclosed comprising a $NaHCO_3$ nanofiber, a $KHCO_3$ nanofiber, or an amino acid nanofiber made from subjecting a $CO_2$ gas to an amino acid aqueous solvent. Preferably, the amino acid aqueous solvent is one or more of a Gly-NaOH—$H_2O$,
(Continued)

an Ala-NaOH—H$_2$O, a Phe-NaOH—H$_2$O, a Gly-KOH—H$_2$O, an Ala-KOH—H$_2$O, and a Phe-KOH—H$_2$O.

5 Claims, 19 Drawing Sheets

(51) Int. Cl.
    *C07C 271/02*     (2006.01)
    *B01D 53/78*     (2006.01)
    *B01D 53/62*     (2006.01)
    *C07C 269/04*     (2006.01)

(52) U.S. Cl.
    CPC ............ *B01D 53/78* (2013.01); *C07C 269/04* (2013.01); *C07C 271/02* (2013.01); *B01D 2251/304* (2013.01); *B01D 2251/306* (2013.01); *B01D 2251/604* (2013.01); *B01D 2251/70* (2013.01); *B01D 2252/20494* (2013.01); *B01D 2252/504* (2013.01); *B01D 2257/504* (2013.01); *B01D 2258/0283* (2013.01); *Y02C 10/04* (2013.01); *Y02C 10/06* (2013.01)

(56) References Cited

U.S. PATENT DOCUMENTS

| | | | | |
|---|---|---|---|---|
| 9,878,285 | B2* | 1/2018 | Schraven | B01D 53/1475 |
| 2006/0117954 | A1* | 6/2006 | Versteeg | B01D 53/1456 95/236 |
| 2008/0125314 | A1* | 5/2008 | Shim | B01D 53/1475 502/401 |
| 2011/0174156 | A1* | 7/2011 | Saunders | B01D 53/1475 95/46 |
| 2012/0282158 | A1* | 11/2012 | Goetheer | B01D 53/1406 423/210 |
| 2014/0318000 | A1* | 10/2014 | Goetheer | A01G 33/00 44/307 |
| 2014/0322803 | A1* | 10/2014 | Constantz | C01B 32/60 435/289.1 |
| 2014/0356268 | A1* | 12/2014 | Schraven | B01D 53/1475 423/228 |
| 2014/0370242 | A1* | 12/2014 | Constantz | C01F 11/181 428/143 |
| 2016/0010142 | A1* | 1/2016 | Salmon | C12Y 402/01001 435/4 |
| 2016/0082387 | A1* | 3/2016 | Constantz | B01D 53/62 405/53 |

OTHER PUBLICATIONS

Yue, M., et al., Temperature-Responsive Microgel Films as Reversible Carbon Dioxide Absorbents in Wet Environment, 2014, Agnew. Chem. Inc. Ed., 2654, vol. 53, Wiley-VCH Verlag GmbH & Co. KGaA, Weinheim.
Pascala, S., et al., Stabilisation Wedges: Solving the Climate Problem for the Next 50 Years with Current Technologies, 2004, Science, 968, vol. 305, No. 5686, The Cambridge-MIT Institute University of Cambridge.
Lin, L., et al., In silico screening of carbon-capture materials, 2012, Nature Materials, 633, vol. 11, Macmillan Publishers Limited.
Keeling, C., et al., Atmospheric carbon dioxide variations at Mauna Loa Observatory, Hawaii, 2014, Tellus, 538, vol. 28i6, Taylor & Francis Group LLC.
Tollefson, J., Growing agricultural benefits for climate, 2009, Nature, 966, vol. 462, Macmillan Publishers Limited.
Department of Energy & Climate Change, A 2030 framework for climate and energy policies, 2013, UK Government Response to Commission Green Paper COM(2013), 169 final, 2014, Crown.

Chu, S., Carbon Capture and Sequestration, 2009, Science, 1599, vol. 325, AAAS.
Gao, W., et al., Crystal Engineering of an nbo Toplogy Metal-Organic Framework for Chemical Fixation of CO2 under Ambient Conditions, 2014, Angew. Chem. Inc. Ed., 2615-2619, vol. 53, Wiley-VCH Verlag GmbH & Co. KGaA, Weinheim.
Mathieu, P., The IPCC Special Report on Carbon Dioxide Capture and Storage, 2006, 1611, Proceedings of ECOS 2006, Aghia Pelagia, Crete, Greece.
Ramezan, M., et al., Carbon Dioxide Capture from Existing Coal-Fired Power Plants, 2007, DOE/NETL-401/110907, National Energy Technology Laboratory, US Department of Energy.
D'Alessandro, D. M., et al., Carbon Dioxide Capture: Prospects for New Materials, 2010, 6058, vol. 49, Angew. Chem. Int. Ed., 2010 Wiley-VCH Verlag GmbH & KGaA, Weinheim.
Yong, Z., et al., Adsorption of Carbon Dioxide on chemically Modified High Surface Area Carbon-Based Adsorbents at High Temperature, 2001, Adsorption 41, vol. 7, Kluwer Academic Publishers.
Li, B., et al., Advances in CO2 capture technology: A patent review, 2013, Applied Energy, 1439-1447, vol. 102, Elsevier Ltd.
Macdowell, N. et al., An overview of CO2 capture technologies, 2010, Energy Environ. Sci., 1645-1669, vol. 3, The Royal Society of Chemistry.
Anderson, S., et al., Prospects for Carbon Capture and Storage Technologies, 2003, Resources for the Future, 2-68, Resources for the Future.
Haszeldine, R. S., Carbon Capture and Storage: How Green Can Black Be?, 2009, Science, 1647, vol. 325, American Association for the Advancement of Science.
Little, M. G., et al., Potential Impacts of Leakage from Deep CO2 Geosequestration on Overlying Freshwater Aquifers, 2010, Environmental Science & Technology, 9225-9232, vol. 44, American Chemical Society.
Kim, S. H., et al., Carbon Dioxide Capture and Use: Organic Synthesis Using Carbon Dioxide from Exhaust Gas, 2014, Angew. Chem. Int. Ed., 771, vol. 53, Wiley-VCH Verlag GmbH & Co. KGaA, Weinheim.
Moret, S., et al., Direct synthesis of formic acid from carbon dioxide by hydrogenation in acidic media, 2014, Nature Communications, 4017, vol. 5, Macmillan Publishers Limited.
Behrens, M., et al., The Active Site of methanol Synthesis over Cu/ZnO/Al2O3 Industrial Catalysts, 2012, Science, 893, vol. 336, American Association for the Advancement of Science.
Damiani, D., et al., The US Department of Energy's R&D program to reduce greenhouse gas emissions through beneficial uses of carbon dioxide, 2011, Greenhouse Gases Science and Technology, 1-11, vol. 1, John Wiley & Sons, Ltd.
Bhaduri, G. A., et al., Nickel nanoparticles catalyse reversible hydration of carbon dioxide for mineralization carbon capture and storage, 2013, Catal. Sci. Technol. 1234-1239, vol. 3, The Royal Society of Chemistry.
Gebreeyessus, G. D., et al., Removing carbon dioxide from a stationary source through co-generation of carbonate/bicarbonate: The case of Mugher cement factory, 2014, African Journal of Environmental Science and Technology, 75-85, vol. 8(1), Academic Journals.
Stauffer, P. H., et al., Greening Coal: Breakthroughs and Challenges in Carbon Capture and Storage, 2011, Environmental Science & Technology, 8597-8604, ACS Publications.
Jiang, B. et al., Development of amino acid and amino acid-complex based solid sorbents for CO2 capture, 2013, Applied Energy, 112-118, vol. 109, Elsevier Ltd.
Wang, X., et al., Immobilization of amino acid ionic liquids into nanoporous microspheres as robust sorbents for CO2 rapture, 2013, J. Mater. Chem, 2978, vol. 1, The Royal Society of Chemistry.
Wang, X., et al., Amino Acid-Functionalized Ionic Liquid Solid Sorbents for Post-Combustion Carbon Capture, 2013, ACS Appl. Mater. Interfaces, 8670-8677, vol. 5, ACS Publications.
Munoz, D. M., et al., New liquid absorbents for the removal of CO2 from gas mixtures, 2009, Energy & Environmental Science, 883-891, vol. 2, The Royal Society of Chemistry.

(56) References Cited

OTHER PUBLICATIONS

Jiang, B., et al., Polypeptide Multilayer Film Co-Delivers Oppositely-Charged Drug Molecules in Sustained Manners, 2010, Biomarcromolecules, 3630-3637, vol. 11, American Chemical Society.

Li, B., et al., Multilayer polypeptide nanoscale coatings incorporation IL-12 for the prevention of biomedical device associated infections, 2009, Biomaterials, 2552-2558, vol. 30(13), Biomaterials.

Jiang, B., et al., Tunable drug loading and release from polypeptide multilayer nanofilms, 2009, International Journal of Nanomedicine, 37-53, vol. 4, Dove Medical Press Ltd.

Jiang, B., et al., Polypeptide Nanocoatings for Preventing Dental and Orthopaedic Device-Associated Infection: pH-Induced Antibiotic Capture, Release, and Antibiotic Efficacy, 2009, J. Biomed Mater Res., Applied Biomater, 332-338, vol. 88B, Wiley Periodicals, Inc.

Jiang, B., et al., Advances in polyelectrolyte multilayer nanofilms as tunable drug delivery systems, 2009, Nanotechnology, Science and Applications, 21-27, vol. 2, Dove Medical Press Ltd.

Knuutila, H., et al., Post combustion CO2 capture with an amino acid salt, 2011, 1550-1557 vol. 4, Energy Procedia, Elsevier Ltd.

Portugal, A. F., et al., Solubility of carbon dioxide in aqueous solutions of amino acid salts, 2009, Chemical Engineering Science, 1993-2002, vol. 64, Elsevier Ltd.

Majchrowicz, M. E., et al., Precipitation regime for selected amino acid salts for CO2 capture from flue gases, 2009, Energy Procedia, 979-84, vol. 1, Elsevier Ltd.

Song, H-J, et al., Carbon dioxide absorption characteristics of aqueous amino acid salt solutions, 2012, International Journal of Greenhouse Gas Control, 64-72, vol. 11, Elsevier Ltd.

Kumar, P. S., et al., Equilibrium Solubility of CO2 in Aqueous Potassium Taurate Solutions: Part 1. Crystallization in Carbon Dioxide Loaded Aqueous Salt Solutions of Amino Acids, 2003, Industrial & Engineering Chemistry Research, 2832-2840, vol. 42, American Chemical Society.

Sanchez-Fernandez, et al., New process concepts for CO2 capture based on precipitating amino acids, 2013, Energy Procedia, 1-12, Elsevier Ltd.

Hook, R. J., An Investigation of Some Sterically Hindered Amines as Potential Carbon Dioxide Scrubbing compounds, 1997, Industrial & Engineering Chemistry Research, 1779-1790, vol. 36, American Chemical Society.

Kumar, P. S., et al., Equilibrium Solubility of CO2 in Aqueous Potassium Taurate Solutions: Part 2. Experimental VLE Data and Model, 2003, Industrial & Engineering Chemistry Research, 2841-2852, vol., American Chemical Society.

Tseng, H. C., et al., Solubilities of amino acids in water at various pH values under 298.15 K, 2009, Fluid Phase Equilibria, 90-95, vol. 285, Elsevier, Ltd.

Dunn, M. S., et al., The Solubility of the Amino Acids in Water, 1933, Journal of Biological Chemistry, 579-595, vol. 103, Chemical Laboratory, University of California at Los Angeles.

Needham, T. E., et al., Solubility of Amino Acids in Pure Solvent Systems, 1971, Journal of Pharmaceutical Science, 365-567, vol. 60, No. 4.

\* cited by examiner

AMINO ACIDS REACT WITH CARBON DIOXIDE (CO2) AND FORM NANOFIBERS AND NANOFLOWERS

CROSS-REFERENCE TO RELATED APPLICATION

This utility non-provisional patent application claims the benefit of U.S. Provisional patent Application Ser. No. 62/345,282, filed on Jun. 3, 2016. The entire contents of U.S. Provisional Patent Application Ser. No. 62/345,282 is incorporated by reference into this utility patent application as if fully written herein.

STATEMENT REGARDING FEDERALLY SPONSORED RESEARCH OR DEVELOPMENT

This invention was made with government support under Grant No. RES DE-FE0004000 awarded by the Department of Energy, DOE/NETL. The government has certain rights in the invention.

BACKGROUND OF THE INVENTION

1. Field of the Invention

The present invention provides (i) nanomaterials such as bicarbonate nanoflowers and nanofibers, and (ii) a method for manufacturing these bicarbonate nanomaterials and amino acid nanofibers using an environmentally friendly approach, and (iii) a process of using these bicarbonate nanomaterials and amino acid nanofibers for capturing $CO_2$ which otherwise would be released into atmosphere such as for example by power generation facilities.

2. Background Art

One of the most promising fields in the manufacturing section is "nanomanufacturing" which has been a growing economy since many industrial sectors (such as aerospace, energy, transportation, and medicine) have been highly benefited and improved by the application of nanomaterials. Most of today's products involving nanomaterials are produced using top down conventional technologies, while the large facilities, needed for large-scale production, have a huge environmental impact. New methods of nanomaterials production that have less environmental impact or reduce environmental concerns are desirable to make nanomanufacturing more attractive to the industrial sector.

Meanwhile, human activity contributes ~35 billion tons of carbon dioxide ($CO_2$), a major greenhouse gas, to the atmosphere every year. The accumulation of $CO_2$ in the atmosphere has been widely believed to be a major contributor to global climate change over decades [1, 2].

Unfortunately, despite the advances in alternative energy, future energy scenarios still include continuing growth in the absolute use of fossil energy[3, 4]. Concerns of the high level (ca. 400 ppm [5, 6]) of $CO_2$ in the atmosphere has therefore resulted in political targets and scientific/technological efforts to reduce $CO_2$ emission. In 2014, the U.S. Environmental Protection Agency proposed a regulation that would cut $CO_2$ emissions from existing coal plants by up to 30 percent by 2030 compared with the 2005 levels, which means cutting 550 million tons of $CO_2$ annually until 2030. The European Commission also proposed a 2030 climate and energy policy framework; a centerpiece of the framework is the target of reducing European Union domestic greenhouse gas emissions by 40% below the 1990 level by 2030 [7]. To achieve these goals, it is imperative that we explore innovative $CO_2$ capture and sequestration (CCS) technologies to reduce $CO_2$ emissions and to lower its concentration in the atmosphere [8, 9].

Most of today's products involving nanomaterials are produced using top down conventional technologies, while most nanomanufacturing process requires advanced and often very expensive equipment and facilities, and the large facilities have a huge environmental impact.

Meanwhile, current carbon capture and sequestration (CCS) technologies are very energy intensive, and $CO_2$ capture dominates in both energy consumption and cost[10, 11]. Aqueous amines and other methods of $CO_2$ capture have been extensively reviewed[12-14]. Among the various $CO_2$ capture technologies, solvent based technologies represent one of the leading options for large scale $CO_2$ capture[15]. Solvents primarily based on aqueous alkanolamine solutions such as monoethanolamine (MEA) are thought to be the most feasible process that may be readily adopted by existing power plants to capture a large amount of $CO_2$ [16]. After $CO_2$ absorption, the aqueous alkanolamine solutions are typically heated to 110° C. or higher to liberate the $CO_2$ for sequestration. This heating demands a high energy input and the subsequent sequestration demands many safe "carbon banks" which so far are limited[17] and may possess potential safety and leakage concerns[18].

A promising strategy to the current CCS technologies is to reduce $CO_2$ emissions via converting $CO_2$ into commercially valuable products[19]. For instance, $CO_2$ may be converted into urea, formic acid, salicylic acid, methanol, etc. [20, 21]; however, catalysts are required and current catalysts have low catalytic activity toward such conversions, and the product separation is difficult. $CO_2$ has also been converted into mineral byproducts such as carbonates and bicarbonates which can be sold or stored without the danger of $CO_2$ leakage and groundwater contamination[22]. In this case, sodium hydroxide (NaOH) has been long studied for removing $CO_2$ through generation of carbonate and bicarbonate in industry. More recently, Skyonic (San Antonio, Tex.) has developed an electrochemical production process to create NaOH to capture $CO_2$ and potentially to sell one of its products (i.e. $NaHCO_3$) as baking soda[22, 23]. However, the NaOH process in general suffers from inefficient mineralization[24].

The combination of $CO_2$ capture and conversion is an attractive strategy for reducing $CO_2$ emission to the atmosphere and meanwhile produces new nanomaterials that have great commercial values. In contrast to the background art, the present invention sets forth an unprecedented strategy, based on self-concentrating amino acids, such as for example but not limited to Glycine and Alanine salt solvents, to convert $CO_2$ into $NaHCO_3$ nanomaterials which are unique and have never been produced or reported. The disclosed invention will overcome problems such as the need for expensive catalysts, difficulty in product separation, and low $CO_2$ capture properties of the previous $CO_2$ conversion approaches. The $NaHCO_3$ and $KHCO_3$ nanomaterials of this invention can also be easily regenerated and reused if desired.

SUMMARY OF THE INVENTION

The present invention provides a method for capturing carbon dioxide comprising dissolving at least one amino acid in water, wherein the amino acid has an amino group located on one end of the amino acid's structure and a carboxyl group located on another end of the amino acid's structure, for protonating the amino group of the amino acid and forming a protonated amino acid, adding a base solution to the protonated amino acid for deprotonating the protonated amino group of the amino acid for forming an amino acid-XOH—$H_2O$ solvent, and subjecting a gas containing carbon dioxide to the amino acid-XOH—$H_2O$ solvent to form a carbamate, wherein X is preferably sodium or potassium. This method preferably includes wherein the base solution is for example, but not limited to, a sodium hydroxide solution or a potassium hydroxide solution.

Another embodiment of this invention includes the method for capturing carbon dioxide, as described herein, wherein the formed carbamate is subjected to hydrolysis to faun $NaHCO_3$ and the absorption of carbon dioxide without the use of a catalyst. This method includes wherein the $NaHCO_3$ is a sodium bicarbonate nanoflower or nanofiber.

Another embodiment of this invention includes the method for capturing carbon dioxide, as described herein, wherein the formed carbamate is subjected to hydrolysis to form potassium bicarbonate and the absorption of carbon dioxide without the use of a catalyst. This method includes wherein the potassium bicarbonate is a potassium bicarbonate nanoflower or nanofiber.

In another embodiment of this invention, a method for capturing carbon dioxide is provided comprising dissolving at least one amino acid in water, wherein the amino acid has an amino group located on one end of the amino acid's structure and a carboxyl group located on another end of the amino acid's structure, for protonating the amino group of the amino acid and forming a protonated amino acid, adding a base solution to the protonated amino acid for deprotonating the protonated amino group of the amino acid for forming an amino acid-XOH—$H_2O$ solvent, and subjecting a gas containing carbon dioxide to the amino acid-XOH—$H_2O$ solvent to form a carbamate, wherein X is preferably sodium or potassium, wherein the amino acid has a formula HOOC—RH—$NH_2$, wherein R is absent or wherein R is an alkyl group having from 1 to 5 carbon atoms, or a substituted alkyl group having from 1 to 5 carbon atoms, wherein the substitutions are one or more side chains or groups of the structures of known twenty amino acids. The known twenty amino acids are glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine. In a preferred embodiment of the method of this invention, the amino acid is selected from the group consisting of alanine (Ala), glycine (Gly) and phenylalanine (Phe). In a more preferred embodiment of the method of this invention, as described herein, the carbon dioxide containing gas is a flue gas, or a waste process stream having carbon dioxide.

Another embodiment of this invention provides a method of absorption of carbon dioxide gas from a process stream comprising subjecting the process stream containing carbon dioxide to a Glycine(Gly)-XOH—$H_2O$ or an Alanine(Ala)-XOH—$H_2O$ without the use of a catalyst to form a carbamate, wherein X is sodium or potassium, for absorption of $CO_2$. In a preferred embodiment of this method, as described herein, X is sodium and includes subjecting the carbamate to undergo hydrolysis to form a sodium bicarbonate ($NaHCO_3$). In a more preferred embodiment of this method, as described herein, the $NaHCO_3$ is in the form of a nanoflower or nanofiber. In another preferred embodiment of this method, as described herein, X is potassium and includes subjecting the carbamate to undergo hydrolysis to form a potassium bicarbonate ($KHCO_3$). In another more preferred embodiment of this method, as described herein, the $KHCO_3$ is in the form of a nanoflower or nanofiber.

Another embodiment of this invention provides a regenerable nanofiber comprising a $NaHCO_3$ nanofiber, a $KHCO_3$ nanofiber, or an amino acid nanofiber made from subjecting a $CO_2$ containing gas to an amino acid aqueous solvent without the use of a catalyst. The regenerable nanofiber of this invention, as described herein, includes wherein the amino acid aqueous solvent is selected from the group consisting of Gly-NaOH—$H_2O$, Ala-NaOH—$H_2O$, Phe-NaOH—$H_2O$, Gly-KOH—$H_2O$, Ala-KOH—$H_2O$, and Phe-KOH—$H_2O$.

Another embodiment of this invention provides a method for producing nanomaterials comprising subjecting a flue gas having carbon dioxide or a carbon dioxide greenhouse gas to an amino acid containing aqueous solution without the use of a catalyst for producing a nanomaterial. This method includes wherein the amino acid containing aqueous solution is selected from the group consisting of Gly-NaOH—$H_2O$, Ala-NaOH—$H_2O$, Phe-NaOH—$H_2O$, Gly-KOH—$H_2O$, Ala-KOH—$H_2O$, and Phe-KOH—$H_2O$. In a preferred embodiment of this method, as described herein, includes wherein the amino acid containing solution is Gly-NaOH—H2O and the resulting nanomaterial is sodium bicarbonate nanomaterial. In a more preferred embodiment of this method, as described herein, the resulting sodium bicarbonate nanomaterial is regenerable and reusable. In another preferred embodiment of this method, as described herein, includes wherein the amino acid containing solution is Gly-K—OH—H2O and the resulting nanomaterial is potassium bicarbonate nanomaterial. In a more preferred embodiment of this method, as described herein, the resulting potassium bicarbonate nanomaterial is regenerable and reusable.

In yet another embodiment of this invention, a solvent is provided comprising at least one amino acid, water, and a base solution, wherein the amino acid(s) is/(are) dissolved in the water and the base solution. In a preferred embodiment of this invention, the solvent, as described herein, wherein the base solution is one selected from a NaOH solution or a KOH solution to form an amino acid-XOH—$H_2O$ solvent wherein X is Na or K. The solvent includes wherein the amino acid is one or more of the amino acids selected from the group of glycine, alanine, serine, threonine, cycteine, valine, leucine, isoleucine, methionine, proline, phenylalanine, tyrosine, tryptophan, aspartic acid, glutamic acid, asparagine, glutamine, histidine, lysine, and arginine. More preferably, the solvent of this invention, as described herein, includes wherein the amino acid is one or more of glycine, alanine, or phenylalanine. In another embodiment of this invention, the solvent, as described herein, is a mixture of two or more of the amino acids. In another embodiment of this invention, the solvent, as described herein, is a mixture of two or more of the amino acids and two or more of the base solutions. In a most preferred embodiment, the solvent of this invention, as described herein, is self-concentrating.

These and other aspects of this invention will be more fully understood from the following detailed description of the invention, the figures, and the claims appended hereto.

BRIEF DESCRIPTION OF THE DRAWINGS

This invention is further illustrated by the following non-limited figures.

DETAILED DESCRIPTION OF THE INVENTION

Figure 1A:
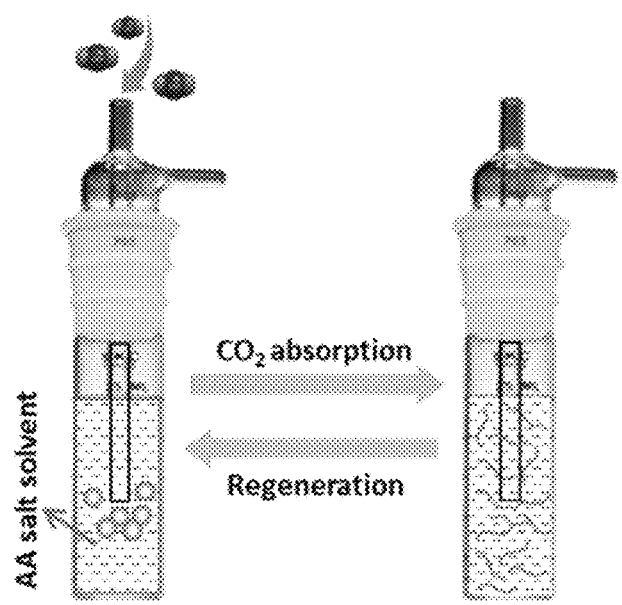
FIG. 1A is a schematic that shows Gly-NaOH—$H_2O$ turns $CO_2$ into regenerable $NaHCO_3$ nano fibers. The schematic shows a cycle of the $CO_2$ absorption and desorption processes of regenerable $NaHCO_3$ nanofibers.

The present invention is directed to a method for capturing carbon dioxide comprising dissolving at least one amino acid in water, wherein the amino acid has an amino group located on one end of the amino acid's structure and a carboxyl group located on another end of the amino acid's structure, for protonating the amino group of the amino acid and forming a protonated amino acid, adding at least one base solution to the protonated amino acid for deprotonating the protonated amino group of the amino acid for forming an amino acid-XOH—$H_2O$ solvent, and subjecting a gas containing carbon dioxide to the amino acid-XOH—$H_2O$ solvent to form a carbamate, wherein X is preferably sodium or potassium. This method preferably includes wherein the base solution is for example, but not limited to, a sodium hydroxide solution or a potassium hydroxide solution.

Another embodiment of this invention includes the method for capturing carbon dioxide, as described herein, wherein the formed carbamate is subjected to hydrolysis to form $NaHCO_3$ and the absorption of carbon dioxide without the use of a catalyst. This method includes wherein the $NaHCO_3$ is a sodium bicarbonate nanoflower or nanofiber.

Another embodiment of this invention includes the method for capturing carbon dioxide, as described herein, wherein the formed carbamate is subjected to hydrolysis to form potassium bicarbonate and the absorption of carbon dioxide without the use of a catalyst. This method includes wherein the potassium bicarbonate is a potassium bicarbonate nanoflower or nanofiber.

In another embodiment of this invention, a method for capturing carbon dioxide is provided comprising dissolving at least one amino acid in water, wherein the amino acid has an amino group located on one end of the amino acid's structure and a carboxyl group located on another end of the amino acid's structure, for protonating the amino group of the amino acid and forming a protonated amino acid, adding at least one base solution to the protonated amino acid for deprotonating the protonated amino group of the amino acid for foaming an amino acid-XOH—$H_2O$ solvent, and subjecting a gas containing carbon dioxide to the amino acid-XOH—$H_2O$ solvent to form a carbamate, wherein X is preferably sodium or potassium, wherein the amino acid has a formula HOOC—RH—$NH_2$, wherein R is absent or wherein R is an alkyl group having from 1 to 5 carbon atoms, or a substituted alkyl group having from 1 to 5 carbon atoms, wherein the substitutions are one or more side chains or groups of the structures of known twenty amino acids. The known twenty amino acids are glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine, in a preferred embodiment of the method of this invention, the amino acid is selected from the group consisting of alanine (Ala), glycine (Gly) and phenylalanine (Phe). In a more preferred embodiment of the method of this invention, as described herein, the carbon dioxide containing gas is a flue gas, or a waste process stream having carbon dioxide.

Another embodiment of this invention provides a method of absorption of carbon dioxide gas from a process stream comprising subjecting the process stream containing carbon dioxide to a Glycine(Gly)-XOH—$H_2O$ or an Alanine(Ala)-XOH—$H_2O$ without the use of a catalyst to form a carbamate, wherein X is sodium or potassium, for absorption of $CO_2$. In a preferred embodiment of this method, as described herein, X is sodium and includes subjecting the carbamate to undergo hydrolysis to form a sodium bicarbonate ($NaHCO_3$). In a more preferred embodiment of this method, as described herein, the $NaHCO_3$ is in the form of a nanoflower or nanofiber. In another preferred embodiment of this method, as described herein, X is potassium and includes subjecting the carbamate to undergo hydrolysis to form a potassium bicarbonate ($KHCO_3$). In another more preferred embodiment of this method, as described herein, the $KHCO_3$ is in the form of a nanoflower or nanofiber.

Another embodiment of this invention provides a regenerable nanofiber comprising a $NaHCO_3$ nanofiber, a $KHCO_3$ nanofiber, or an amino acid nanofiber made from subjecting a $CO_2$ containing gas to an amino acid aqueous solvent without the use of a catalyst. The regenerable nanofiber of this invention, as described herein, includes wherein the amino acid aqueous solvent is selected from the group consisting of Gly-NaOH—$H_2O$, Ala-NaOH—$H_2O$, Phe-NaOH—$H_2O$, Gly-KOH—$H_2O$, Ala-KOH—$H_2O$, and Phe-KOH—$H_2O$.

Another embodiment of this invention provides a method for producing nanomaterials comprising subjecting a flue gas having carbon dioxide or a carbon dioxide greenhouse gas to an amino acid containing aqueous solution without the use of a catalyst for producing a nanomaterial. This method includes wherein the amino acid containing aqueous solution is selected from the group consisting of Gly-NaOH—$H_2O$, Ala-NaOH—$H_2O$, Phe-NaOH—$H_2O$, Gly-KOH—$H_2O$, Ala-KOH—$H_2O$, and Phe-KOH—$H_2O$. In a preferred embodiment of this method, as described herein, includes wherein the amino acid containing solution is Gly-NaOH—H2O and the resulting nanomaterial is sodium bicarbonate nanomaterial. In a more preferred embodiment of this method, as described herein, the resulting sodium bicarbonate nanomaterial is regenerable and reusable. In another preferred embodiment of this method, as described herein, includes wherein the amino acid containing solution is Gly-K—OH—H2O and the resulting nanomaterial is potassium bicarbonate nonmaterial. In a more preferred embodiment of this method, as described herein, the resulting potassium bicarbonate nanomaterial is regenerable and reusable.

In yet another embodiment of this invention, a solvent is provided comprising at least one amino acid, water, and a base solution, wherein the amino acid(s) is (are) dissolved in the water and the base solution. In a preferred embodiment of this invention, the solvent, as described herein, wherein the base solution is one selected from a NaOH solution or a KOH solution to form an amino acid-XOH—$H_2O$ solvent wherein X is Na or K. The solvent includes wherein the amino acid is one or more of the amino acids selected from the group of glycine, alanine, serine, threonine, cycteine, valine, leucine, isoleucine, methionine, proline, phenylalanine, tyrosine, tryptophan, aspartic acid, glutamic acid, asparagine, glutamine, histidine, lysine, and arginine. More preferably, the solvent of this invention, as described herein, includes wherein the amino acid is one or more of glycine, alanine, or phenylalanine. In another embodiment of this invention, the solvent, as described herein, is a mixture of two or more of the amino acids. In another embodiment of this invention, the solvent, as described herein, is a mixture of two or more of the amino acids and two or more of the base solutions. In a most preferred embodiment, the solvent of this invention, as described herein, is self-concentrating.

Those persons skilled in the art will understand that the present invention provides (i) new nanomaterials such as for example but not limited to bicarbonate nanoflowers and nanofibers, which have never been produced, and (ii) a method for manufacturing these nanomaterials using an environmentally friendly approach including where we can manufacture bicarbonate nanomaterials and amino acid nanofibers and simultaneously capture $CO_2$, which otherwise would be released into atmosphere, from power generation facilities (i.e. power plants). In one case (i.e. the production of bicarbonate nanomaterials), the $CO_2$ is actually converted into a commercially useful product. Our new nanomanufacturing approach is performed entirely in an aqueous (no organic solvent) environment while utilizing little to literally no energy.

We have invented the approach to produce sodium bicarbonate nanoflowers and nanofibers, and this approach can be used to produce other nanomaterials such potassium bicarbonate, calcium bicarbonate, etc. We also produced amino acid nanofibers which could be 3D aligned nanofibers.

In other words, to reduce $CO_2$ emission from power plants etc., we developed innovative $CO_2$ capture and utilization technologies to (i) turn $CO_2$ into $NaHCO_3$ nanofibers and nanoflowers, (ii) self concentrate $NaHCO_3$ nanomaterials for easy separation and reuse, and (iii) develop an approach that will lead to both $CO_2$ absorption and amino acid nanofiber formation. Our technology will capture $CO_2$ and convert it into commercial products.

For the first time, $CO_2$ will be converted into nanomaterials and the conversion does not need any catalysts. The present process is simple, environmentally friendly, and is very unique. The present invention contributes significantly to the safe and economical capture of $CO_2$ from flue gas and meets the government's goal to reduce U.S. greenhouse gas emissions by up to 30 percent by 2030 compared with the 2005 levels. The methods of the present invention also produce new important nanomaterials that have great commercial value besides reducing $CO_2$ emission.

Advantages of the Present Invention

First, we have invented a new approach to produce nanomaterials such as bicarbonates which have never been produced by any other approaches. Our new nanomanufacturing approach is performed entirely in an aqueous (no organic solvent) environment while utilizing little to literally no energy. Such a technology is cost effective and environmentally friendly.

Our new nanomanufacturing technology meanwhile allows us to achieve $CO_2$ capture and utilization at the same time; specifically, we provide a self-concentrating amino acid (SCAA) solvent that turns $CO_2$ emission into $NaHCO_3$ nanofibers or nanoflowers, which have great commercial potential. This unique self-concentrating solvent enables us to obtain high $CO_2$ capture capacity and commercially valuable chemicals, offering a great benefit for a real $CO_2$ capture process. By adapting this process to the absorption of $CO_2$ from waste streams, or process streams, significant advantages over current technologies ensue, for example, but not limited to:

(A) Use $NaHCO_3$ nanofibers and nanowires as the final products (i.e. $CO_2$ conversion and utilization):
  i. For the first time, this technology converts $CO_2$ emission into unique $NaHCO_3$ nanofibers and nanoflowers with high $CO_2$ capacity.
  ii. Unlike processes that physically remove the $CO_2$ to a remote site[25] the industrial-scale generation of sodium bicarbonate directly converts the undesirable $CO_2$ gas into nanomaterials or chemicals at the point of power-generation. Because the by-products of the $CO_2$ capture process are economically useful, the value of these products offsets the costs of capture; in properly designed systems, the capture process can become profitable in itself. Unlike aqueous amine-based solvents, which require heating to regenerate the solvent, our technique involves the production of beneficial products, which does not require any regeneration energy.
  iii. In the literature, $CO_2$ may be converted into urea, formic acid, salicylic acid, methanol, etc. [20, 21], however, catalysts are required while current catalysts have low catalytic activity toward such conversions, and the product separation is difficult. In this disclosure, $CO_2$ is converted into $NaHCO_3$ nanomaterials without the use of catalysts. Moreover, the self-concentrating property enables easy separation of the converted products.

(B) Regenerate the produced $NaHCO_3$ nanofibers and nanowires and reuse the materials for multiple cyclic $CO_2$ capture (i.e. capture $CO_2$ for CCS):
  i. Unlike other decarbonation efforts that are not amenable to retrofitting, embodiments of the present system may be retrofitted to existing power-plants, greatly lowering the capital costs necessary to remove $CO_2$. In addition, the $CO_2$ capture processing is scalable (from pilot scale to intermediate scale to full scale implementation) by the addition of incremental reactor units.
  ii. Compared to monoethanolamine (MEA) solvents, the proposed amino acid (AA) salt solutions typically have significantly lower vapor pressures thereby resulting in reduced solvent loss. Furthermore, AA salts typically have greater resistance to oxidative degradation and lower toxicity than typical alkanolamine solvents.[26,28]
  iii. Compared to NaOH scrubbing, the SCAA solvent process has converted $CO_2$ into unique $NaHCO_3$ nanoflowers and has shown a higher $CO_2$ capacity and faster absorption, which may reduce the size of reactors and materials handling equipment, thereby lowering capital costs.[29]
  iv. The produced $NaHCO_3$ could be regenerated at much lower temperatures where biocatalysts can be better applied compared to current technologies.

(C) Fabrication of amino acid nanofibers through a process that captures $CO_2$:
  i. Besides $CO_2$ absorption, high quality and large quantities of amino acid nanofibers can be produced and may serve as commercial products. The process is simple. Again, amino acids have their advantages (e.g. stability) as compared to other materials.

The use of this invention is not restricted to carbon capture. For example but not limited to, it may also be applied to:
  (i) A simple new method to produce nanomaterials. Nanomaterials such as $NaHCO_3$ nanofibers and nanoflowers can be synthesized by simply bubbling acidic greenhouse gases such as $CO_2$ or a simulated flue gas into Glycine and Alanine solutions.
  (ii) A new process to produce high-purity soda nanomaterials. By taking advantage of the unique self-concentrating phenomenon, high-purity soda could be obtained via a simple rinsing procedure (see FIG. 6).
  (iii) A process to simultaneously capture $CO_2$ and obtain amino acid nanofibers. By taking advantage of the self-assembly properties of certain amino acids, easy formation and separation of amino acid nanofibers and $NaHCO_3$ solids can be achieved.
  (iv) A new method to produce inorganic and organic nanomaterials.
  (v) Converting $CO_2$ without the use of catalysts. In the literature, $CO_2$ may be converted into urea, formic acid, salicylic acid, or methanol; however, catalysts are required while current catalysts have low catalytic activity toward such conversions, and the product separation is difficult. In this disclosure, $CO_2$ is converted into $NaHCO_3$ nanomaterials without the use of catalysts. Moreover, the self-concentrating property enables easy separation of the converted products.

Data and Results

The self-concentrating amino acid (SCAA) solvent of this invention was used to turn $CO_2$ into $NaHCO_3$ nanomaterials or baking soda. The work was based on the use of biological materials (amino acids, peptides, proteins, etc.) that we have studied in the context of drug delivery research (controlled and targeted drug capture and release).[30-34]

Materials used in the examples are: $CO_2$ gas, amino acids (for example, but not limited to, Gly, Ala, and Phe), and NaOH.

Solvent Preparation and the Mechanism of $CO_2$ Capture.

In the SCAA (self-concentrating amino acid) process, one or more amino acids (AAs) are used for the absorption of $CO_2$. When a pure amino acid (AA), with the overall formula $HOOC-R-NH_2$, is dissolved in water, the following equilibria are established:[35-38]

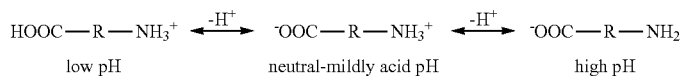

It is thus seen that, in solution, the neutral molecule takes the form of a dipole, because the carboxylic group loses a proton while the amine group is protonated. To absorb $CO_2$, the AAs are first neutralized with a base, for example but not limited to, a NaOH solution or a KOH solution. The base of NaOH is used below, for example:

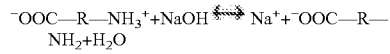

The neutralized AA can then react with $CO_2$ in much the same way as "normal" amines, i.e. forming carbamate and/or bicarbonate:

Carbamate Formation:

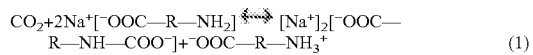 (1)

Carbamate Hydrolysis and Bicarbonate Formation:

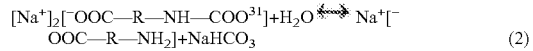 (2)

Therefore, the addition of a base, as described above, is required and its role is to deprotonate the protonated amino group. After deprotonation, AAs react with $CO_2$ to form carbamate, which further undergoes hydrolysis to form $NaHCO_3$. As a result, $CO_2$ is absorbed.

Experimental Feasibility

We examined the absorption of $CO_2$ by Glycine(Gly)-NaOH—$H_2O$ and Alanine(Ala)-NaOH—$H_2O$ first in 100% $CO_2$ followed by experiments in a simulated flue gas.

Figure 1B:
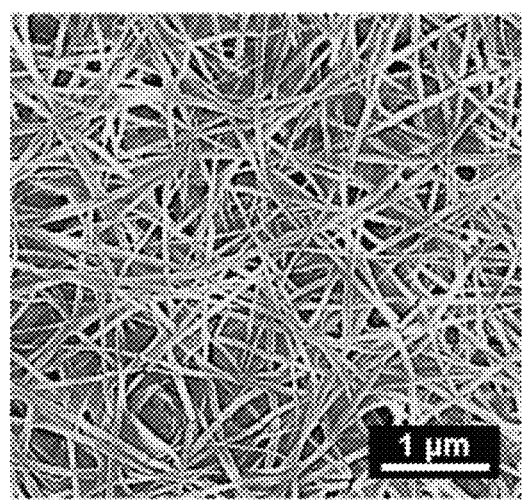
FIG. 1B is a field emission scanning electron microscope (FE-SEM) image of nanofibers obtained in Gly-NaOH—$H_2O$ solution. The $CO_2$ absorption time was 25 minutes.
Figure 1C:
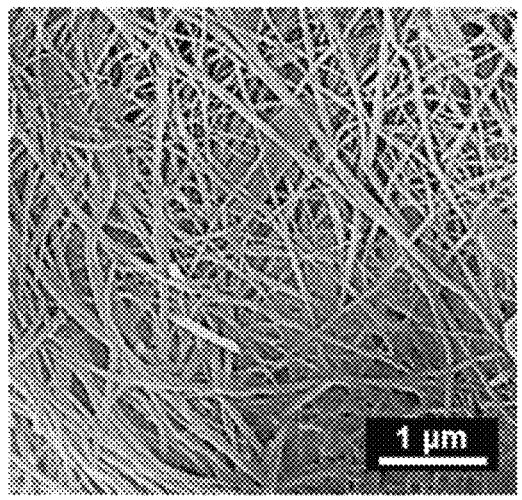
FIG. 1C is a FE-SEM image of Gly-NaOH—$H_2O$ solution after $CO_2$ absorption, desorption, and re-absorption.
Figure 1D:
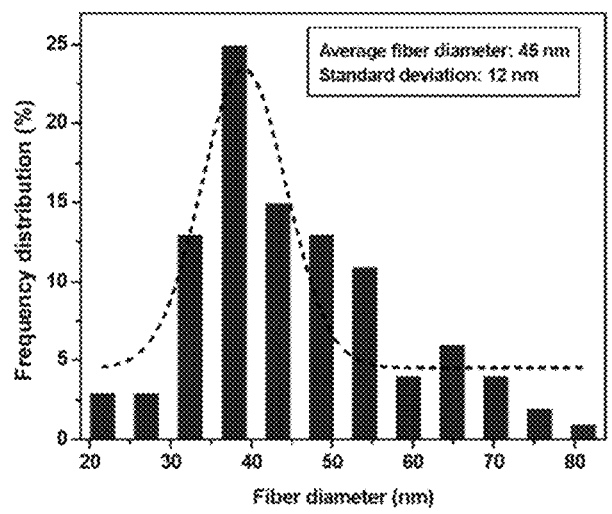
FIG. 1D is a histogram showing the diameter distribution of $NaHCO_3$ nanofibers presented in (FIG. 1B).
Figure 1E:
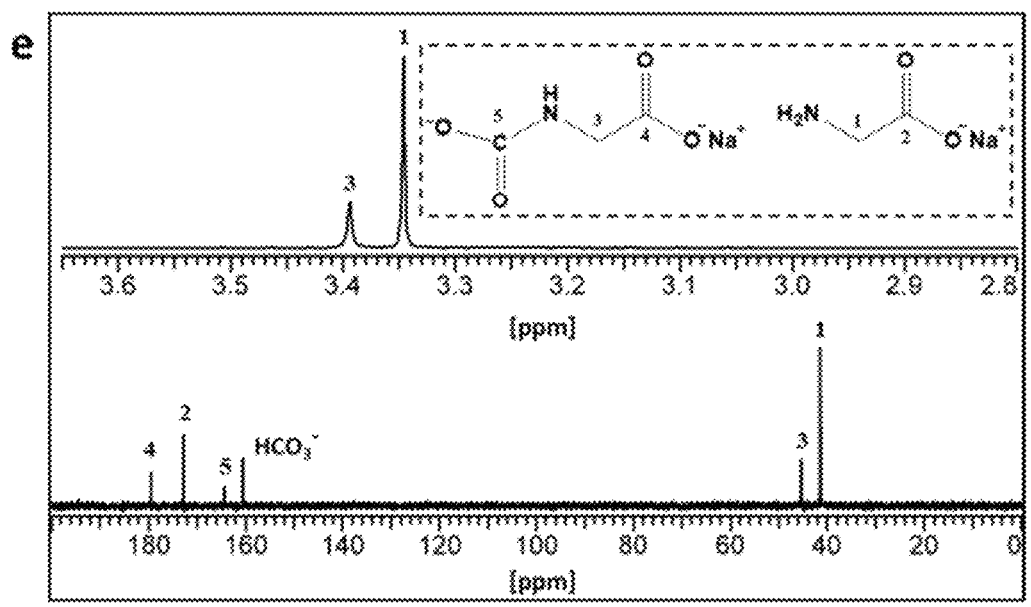
FIG. 1E is a $^1H$ NMR (upper) and $^{13}C$ NMR (lower) spectra of Gly-NaOH—$H_2O$ solution after $CO_2$ absorption.
Figure 1F:
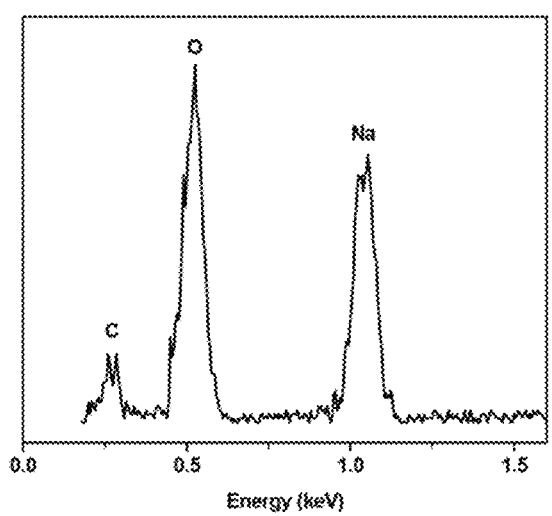
FIG. 1F is an EDX spectrum of single $NaHCO_3$ nanofibers.

(1) Gly-NaOH—$H_2O$ turns $CO_2$ into regenerable $NaHCO_3$ nanofibers:

CO2 was bubbled (FIG. 1A) into Gly-NaOH—$H_2O$ solution for 25 minutes (min). For the first time, long nanofibers were formed in the Gly-NaOH—$H_2O$ solution (FIG. 1B). The nanofibers were tens of micrometers long and their average diameter was about 45 nanometer (nm); the majority (over 80%) of the nanofibers were in the range of 30-55 nm (FIG. 1D). Nuclear magnetic resonance (NMR) studies found that $NaHCO_3$, Gly/GlyH$^+$, and Gly carbamate were presented in the Gly-NaOH—$H_2O$ solution upon $CO_2$ absorption (FIG. 1E). Further characterization of the nanofibers by energy dispersive X-ray (EDX) spectroscopy found sodium, oxygen, and carbon but no nitrogen in the nanofibers (FIG. 1F). These NMR and EDX studies suggested that the nanofibers were $NaHCO_3$. These findings mean that $CO_2$ can be converted into inorganic nanofibers, for example but not limited to $NaHCO_3$ nanofibers (i.e. bubbling $CO_2$ in Gly-NaOH—$H_2O$ solutions), allowing easy production of inorganic nanofibers while reducing $CO_2$ emission. $NaHCO_3$ solids usually exist in the form of crystals and, to our knowledge, no $NaHCO_3$ nanoparticles or nanofibers have even been reported in the literature.

Figure 1G:
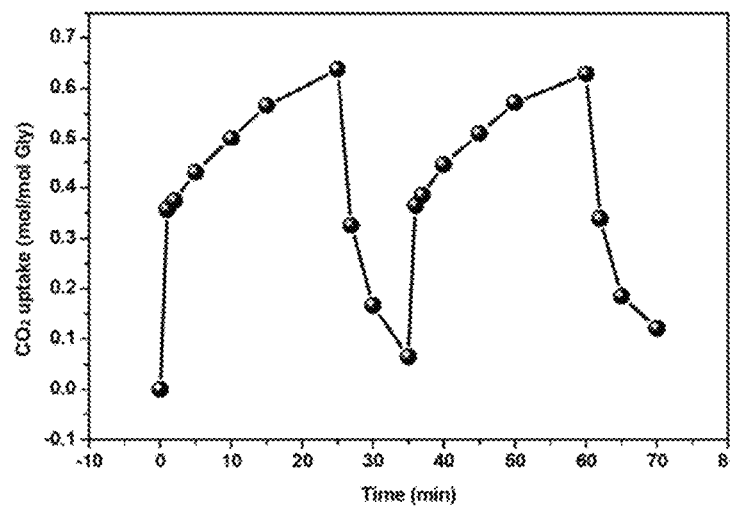
FIG. 1G shows a cyclic $CO_2$ absorption and desorption performance of Gly-NaOH—$H_2O$ solution.

Interestingly, we found that the $NaHCO_3$ nanofibers could be easily regenerated in the Gly-NaOH—$H_2O$ solution. After heating the solution (after $CO_2$ absorption) at 383K for 10 min (minutes), no nanofibers were observed. However, $NaHCO_3$ nanofibers were formed again (FIG. 1C) after bubbling $CO_2$ in the regenerated Gly-NaOH—$H_2O$ solution. It seems that the Gly-NaOH—$H_2O$ solution had a two-stage $CO_2$ absorption: In the first stage, the $CO_2$ absorption capacity increased very quickly and reached a capacity of [(0.37 mol $CO_2$)/(mol Gly)] within the first 2 min, and in the second absorption stage, the $CO_2$ absorption continued to increase but at a much slower rate compared to that of the first stage (FIG. 1G). A significant capacity of [–(0.64 mol $CO_2$)/(mol Gly)] was obtained and the solution could be regenerated and reused (FIG. 1G). Therefore, Gly-NaOH—$H_2O$ solution could be used to absorb $CO_2$ while producing $NaHCO_3$ nanofibers and could be easily regenerated with a thermal swing process. Note that no $NaHCO_3$ specie was observed in the Gly-NaOH—$H_2O$ solution after $CO_2$ absorption; this may indicate that, in the Gly-NaOH—$H_2O$ solution, it is difficult for NaOH to react with $CO_2$ to form $Na_2CO_3$, which is the main product if NaOH dissolved in $H_2O$ alone is used to absorb $CO_2$.

Figure 2A:
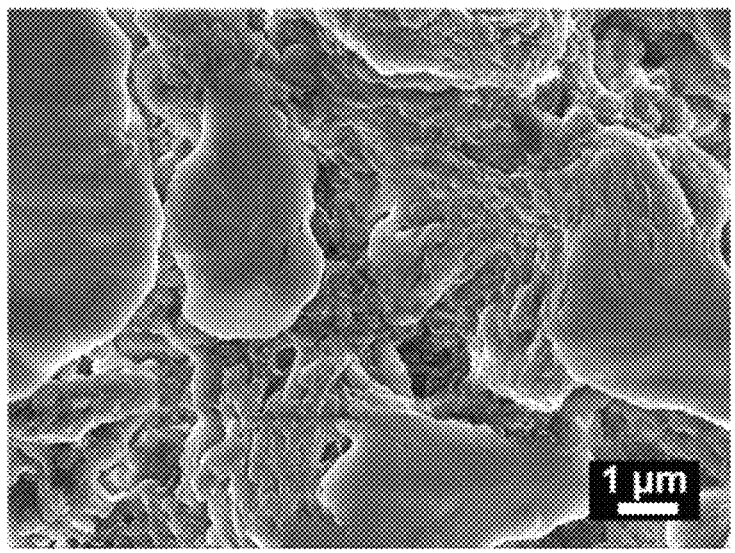
FIG. 2A is a SEM image that shows the effect of $CO_2$ absorption time on formation of $NaHCO_3$ nanofibers, specifically, a SEM image at $CO_2$ absorption of 2 minutes.
Figure 2B:
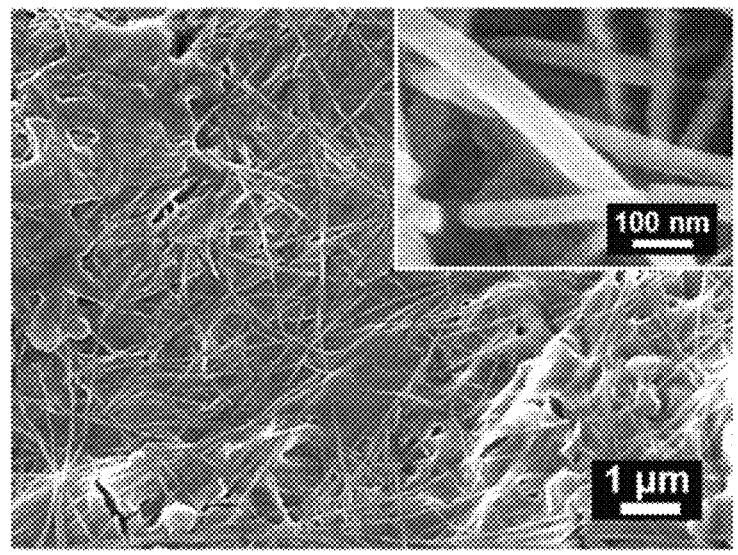
FIG. 2B is an SEM image at $CO_2$ absorption of 5 minutes.
Figure 2C:
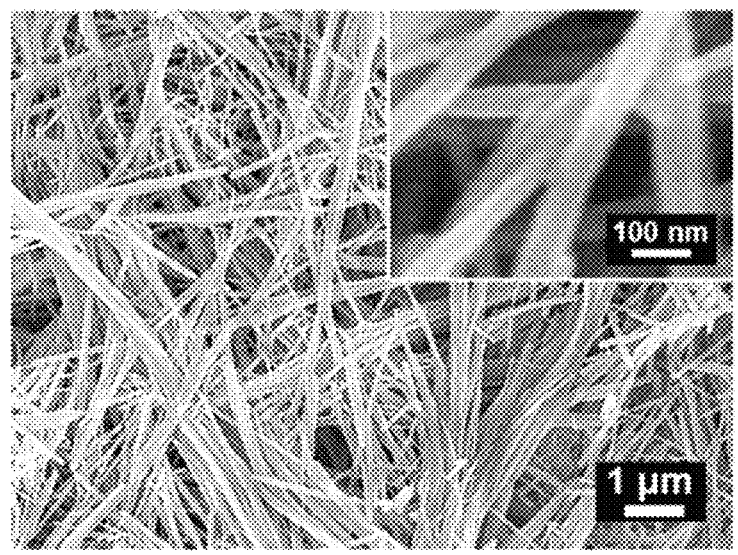
FIG. 2C is an SEM image at $CO_2$ absorption of 10 minutes.
Figure 2D:
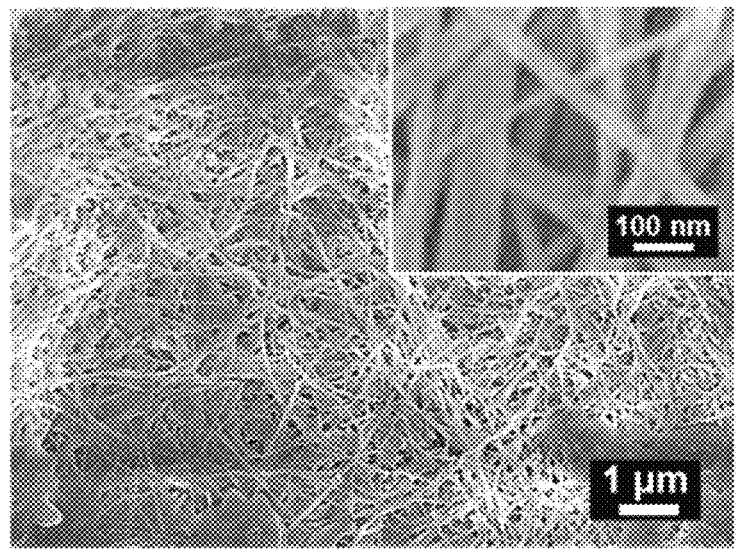
FIG. 2D is an SEM image at $CO_2$ absorption of 15 minutes.
Figure 2E:
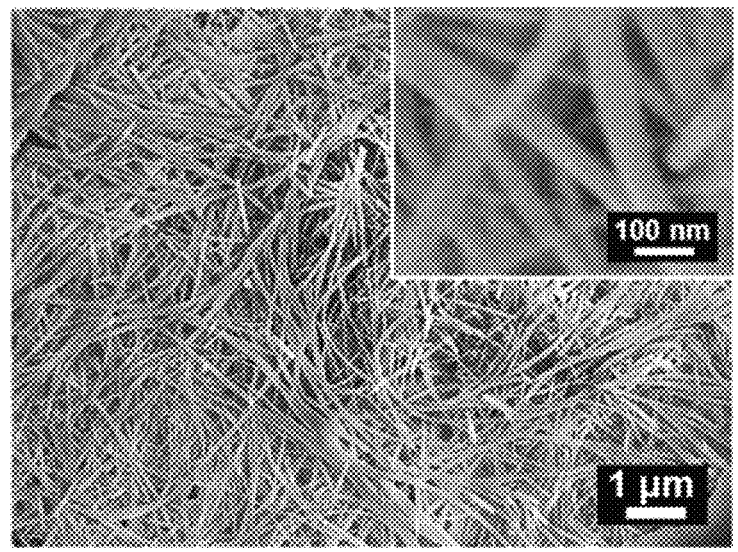
FIG. 2E is an SEM image at $CO_2$ absorption of 25 minutes.
Figure 2F:
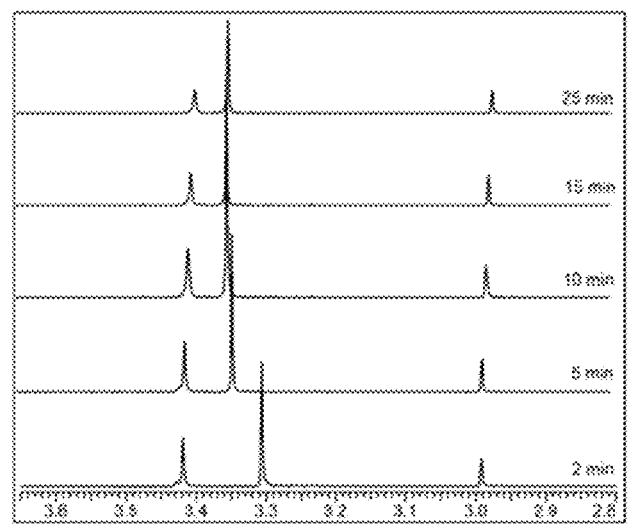
FIG. 2F is an SEM image at $CO_2$ absorption of $^1H$ NMR.
Figure 2G:
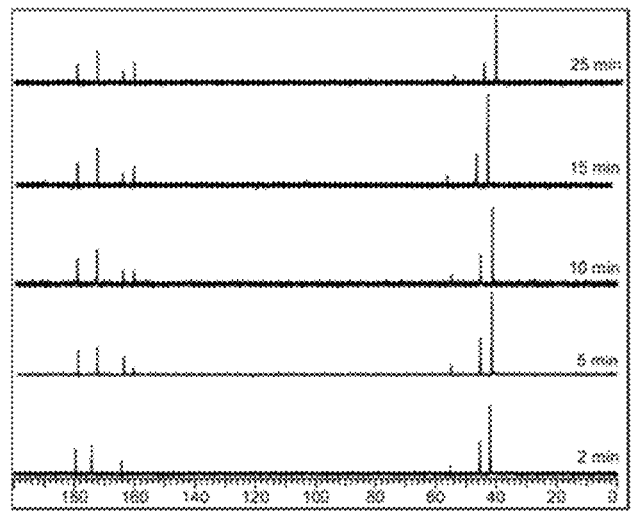
FIG. 2G is an SEM image at $CO_2$ absorption of $^{13}C$ NMR spectra for Gly-NaOH—$H_2O$ solution at varying absorption time. Tetramethylammonium chloride [(CH])4N$^+$Cl], used as a standard reference for quantitative determination of species, shows peaks at 3.05 and 55.10 ppm in $^1H$ NMR and $^{13}C$ NMR spectra, respectively.
Figure 2H:
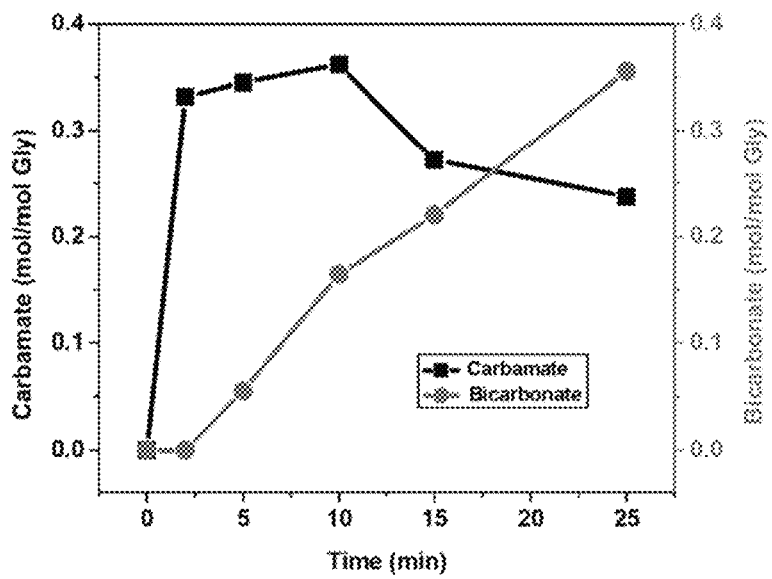
FIG. 2H shows species changes in Gly-NaOH—$H_2O$ solution as a function of $CO_2$ absorption time from NMR spectra.

We further performed FE-SEM and NMR studies to examine $NaHCO_3$ nanofiber formation and species changes in the Gly-NaOH—$H_2O$ solution as a function of $CO_2$ absorption time (FIGS. 2A-H). No $NaHCO_3$ nanofibers were observed before 2 min (FIG. 2A), nanofibers were formed at 5 min (FIG. 2B), and more $NaHCO_3$ nanofibers were produced with further increasing $CO_2$ absorption time (FIG. 2B-E). Correspondingly, NMR data showed that no $NaHCO_3$ species were detected before 2 min, while $NaHCO_3$ was formed at 5 min and kept increasing with increasing $CO_2$ absorption time (FIGS. 2F-H). Meanwhile, the amount of Gly carbamate increased sharply from 0 to 2 min, then increased at a much slower rate (compared to the first 2 min) with increasing $CO_2$ absorption time during 2-10 min, after which the amount of Gly carbamate decreased with further increasing $CO_2$ absorption time (FIG. 2F-H).

Figure 3A:
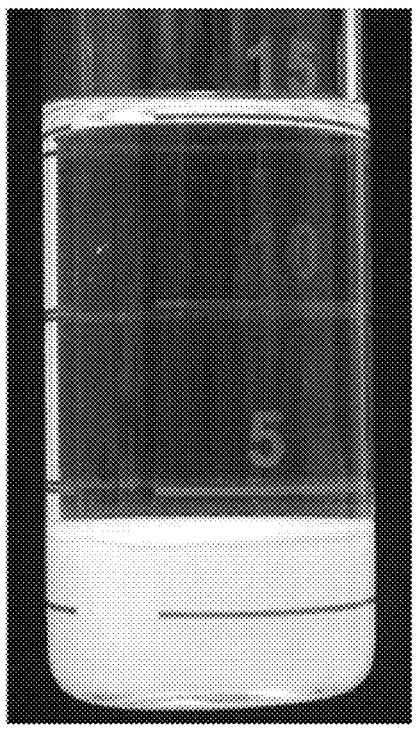
FIG. 3A is an image of Ala-NaOH—$H_2O$ solution after $CO_2$ absorption.
Figure 3B:
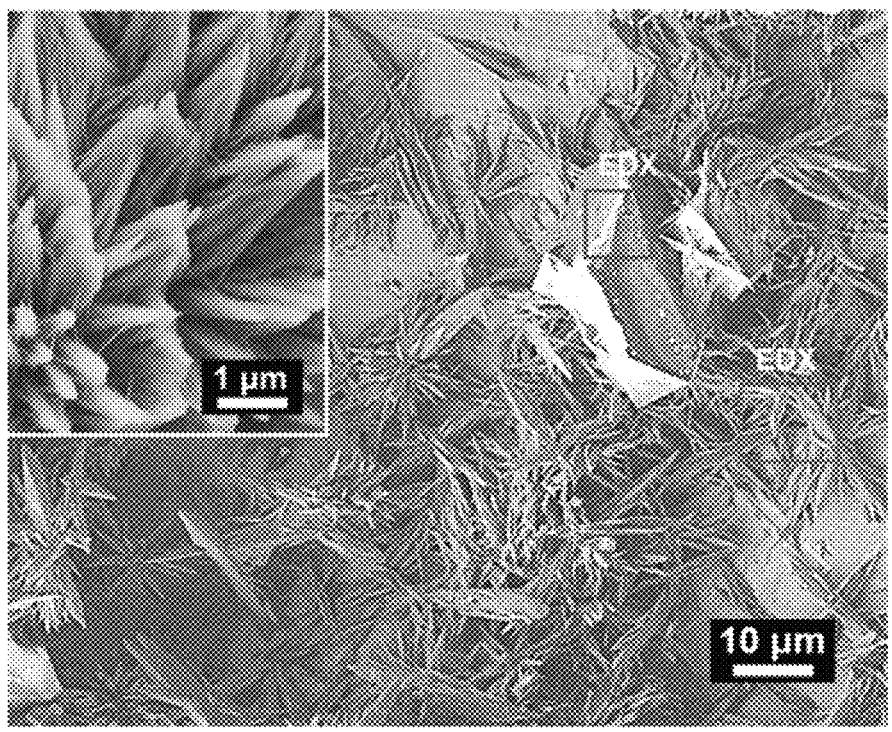
FIG. 3B is an typical FE-SEM image of solid precipitates formed in self-concentrating Ala-NaOH—$H_2O$ solution. Inset shows a high-resolution FE-SEM image of a flower of $NaHCO_3$ nanowires.
Figure 3C:
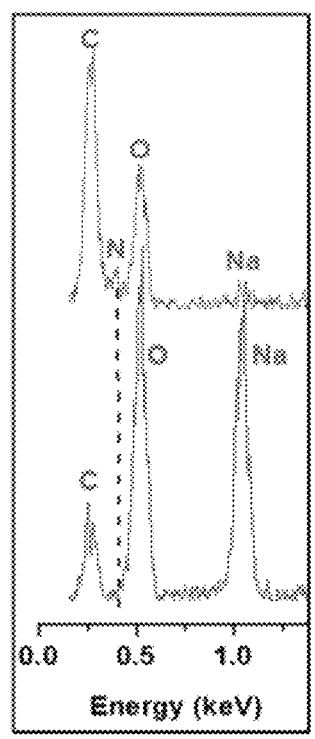
FIG. 3C is an EDX spectra of Ala particles (Lipper) and $NaHCO_3$ nanowires (lower).
Figure 3D:
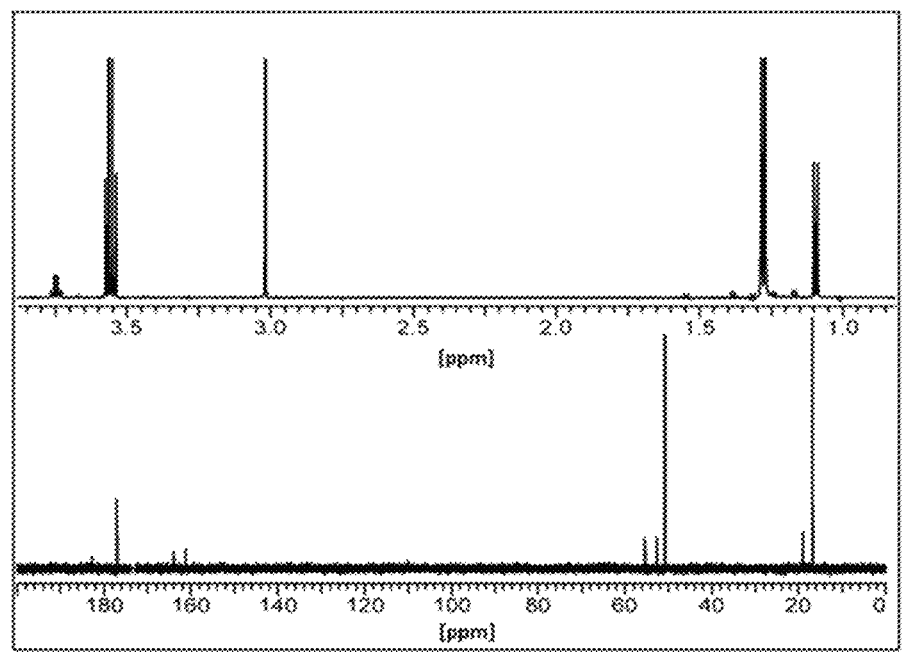
FIG. 3D is a $^1H$ NMR (upper) and $^{13}C$ NMR (lower) spectra of lean phase. Tetramethylammonium chloride [(CH3)4N$^+$Cr] was used as a standard reference.
Figure 3E:
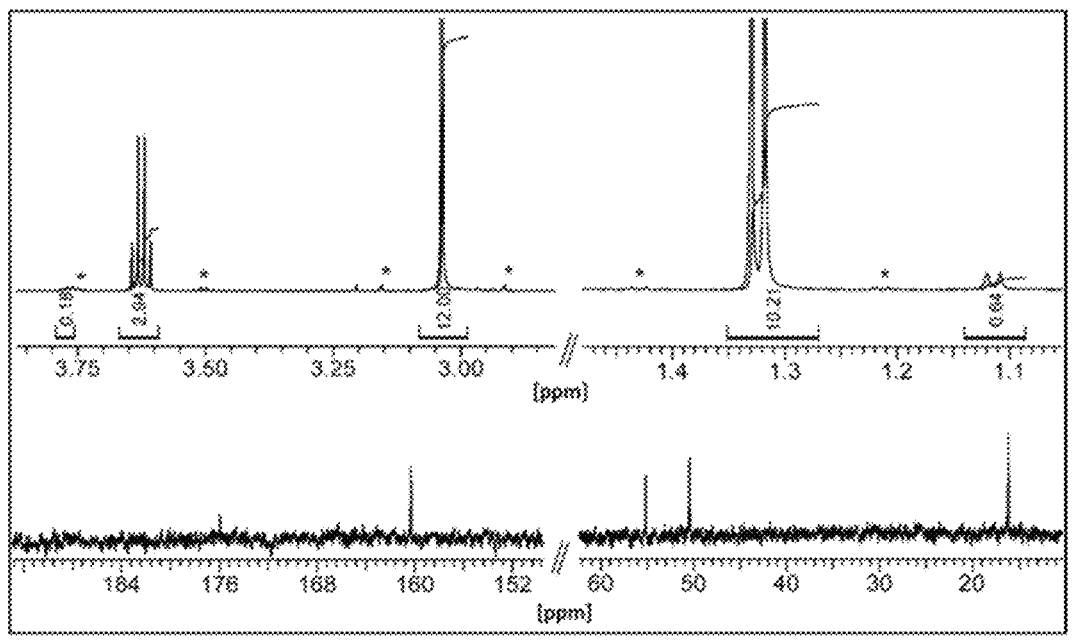
FIG. 3E is a $^1H$ NMR (upper) and $^{13}C$ NMR (lower) spectra of solid mixes.

(2) In 100% $CO_2$, Alanine (Ala) salt solution converted $CO_2$ into $NaHCO_3$ nanoflowers and had high $CO_2$ absorption performance:

We found that Ala-NaOH—$H_2O$ solution formed, after bubbling with 100% $CO_2$, two "phases" with the top clear phase (~½ in volume) and the bottom "milky" phase (~½ in volume. FIG. 3A). FE-SEM and elemental (EDX) analyses found that the "milky" phase had $NaHCO_3$ nanoflowers and Ala particles (FIGS. 3B and 3C). The nanoflowers were comprised of bunches of $NaHCO_3$ nanowires, which were about (~) 50 nm in diameter and about 15 μm in length (FIG. 3B). Nuclear magnetic resonance (NMR) studies showed that $NaHCO_3$, Ala/AlaH$^+$, and Ala carbamate were found in both the clear phase and the "milky" phase (FIGS. 3D and 3E). In the solid mixes, $NaHCO_3$ was dominant and the amounts of $NaHCO_3$, Ala/AlaH$^+$, and Ala carbamate were 73.5, 23.5, and 3.0 wt %, respectively (FIG. 3E). In the clear phase, Ala/AlaH$^+$ was dominant and the amounts of $NaHCO_3$, Ala/AlaH$^+$, and Ala carbamate were about 15.0, about 65.0, and about 20.0 wt %, respectively (FIG. 3D).

Figure 4:
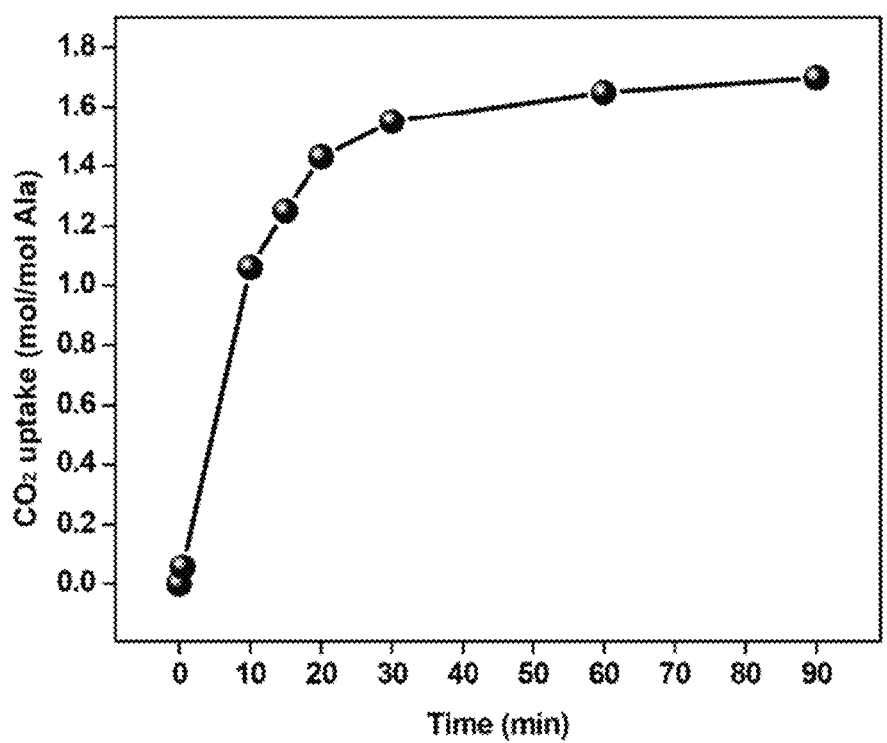
FIG. 4 shows $CO_2$ uptake performance of Ala-NaOH—$H_2O$ solvent of this invention.

A two-stage $CO_2$ absorption was observed in Ala-NaOH—$H_2O$ solution: The $CO_2$ absorption capacity increased sharply first followed with a much slower $CO_2$ absorption before it plateaued (FIG. 4). The $CO_2$ absorption capacity of Ala-NaOH—$H_2O$ solution (including the two phases) was found to be (1.78 mol $CO_2$)/(mol Ala) (FIG. 4). Note that the formation of the solids, which shifts the equilibrium of the reactions (1) and (2) toward the formation of carbamate or bicarbonate, likely have contributed to the high $CO_2$ absorption capacity. This is consistent with the observations by Kumar et al. who achieved higher $CO_2$ absorption capacity when amino acid precipitated.[39] Interestingly, over 90% of the $CO_2$ absorbed by the Ala-NaOH—$H_2O$ solution was in the "milky" phase and the majority (~95%) of the $CO_2$ was absorbed in the form of $NaHCO_3$ nanoflowers. In other words, Ala-NaOH—$H_2O$ solution self-concentrated into a $CO_2$-lean phase (i.e. the clear phase) and a $CO_2$-rich phase (i.e. the "milky" phase) upon bubbling with $CO_2$.

Figure 5:
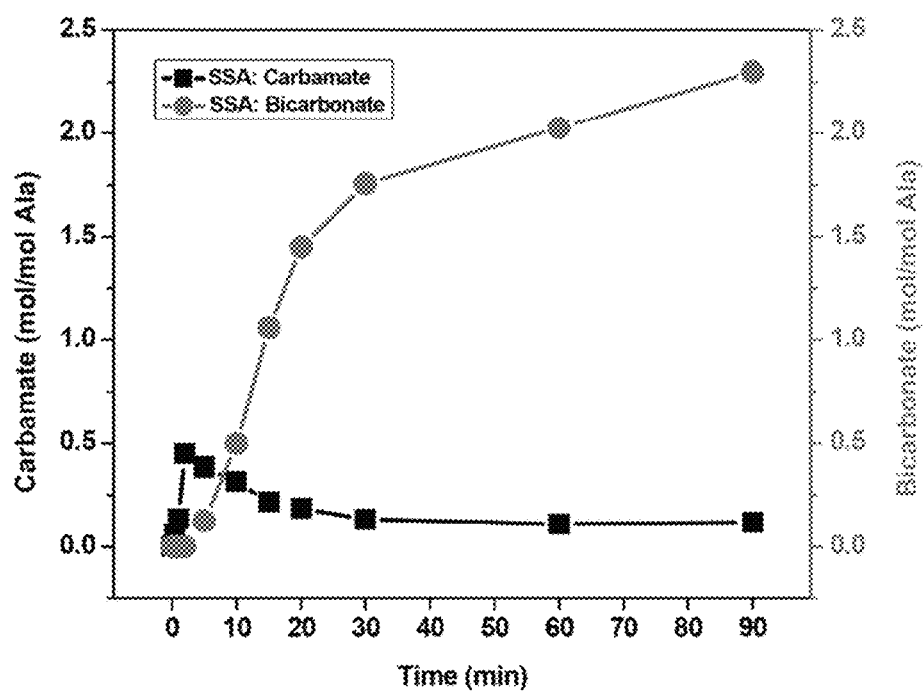
FIG. 5 shows species changes (from NMR spectra) in Ala-NaOH—$H_2O$ as a function of $CO_2$ absorption time.

NMR spectra at different $CO_2$ absorption times revealed that Ala carbamate formed immediately after bubbling $CO_2$ into Ala-NaOH—$H_2O$ solution, and the amount of Ala carbamate increased sharply from 0 to 2 min and then decreased with increasing CO2 absorption time (FIG. 5). No $NaHCO_3$ was detected before 2 min. $NaHCO_3$ started to form at 5 min and its amount increased rapidly from 5 to 30 min followed by an increase at a much slower rate from 30 to 90 min with increasing $CO_2$ absorption time (FIG. 5). At 30 min, there were ~1.75 mol/(mol Ala) of $NaHCO_3$ and ~0.13 mol/(mol Ala) of Ala carbamate (FIG. 5). Obviously, $CO_2$ reacted first with Ala in the Ala-NaOH—$H_2O$ solution to form Ala carbamate which later hydrolyzed into $NaHCO_3$, in agreement with the aforementioned reactions (1) and (2).

Solid precipitates have been reported in some AAs when they interact with $CO_2$. Different precipitates have been reported depending on the AA structures and solubilities.[37,40] For instance, Hook first reported the formation of carbonate precipitates in aqueous potassium salts of N-methylalanine and α-aminoisobutyric acid (and their sterically hindered derivatives) upon reacting with $CO_2$.[41] Versteeg and co-workers found that, upon interacting with $CO_2$, AAs (e.g. taurine) formed precipitates of AA zwitterions and possibly a small portion of bicarbonate.[42] Precipitation of AAs are due to the decrease of pH during $CO_2$ bubbling since the solubility of AAs decreases with decreasing pH. To our knowledge, however, none of the previous studies had formed $NaHCO_3$ nanoflowers and there was no clear separation of the $CO_2$-lean and $CO_2$-rich phases. Therefore the unique characteristics of the Ala-NaOH—$H_2O$ solution presented here include (i) the formation of $NaHCO_3$ nanoflowers and the majority of the $CO_2$ absorbed was in the form of $NaHCO_3$; nanoflowers, (ii) the clear separation of the $CO_2$-lean and $CO_2$-rich phases, (iii) the $CO_2$-rich phase having over 90% of the $CO_2$ absorbed by the whole solution, and (iv) the $CO_2$-rich phase possessing a small volume (i.e. ~½ of the total volume).

Figure 6A:
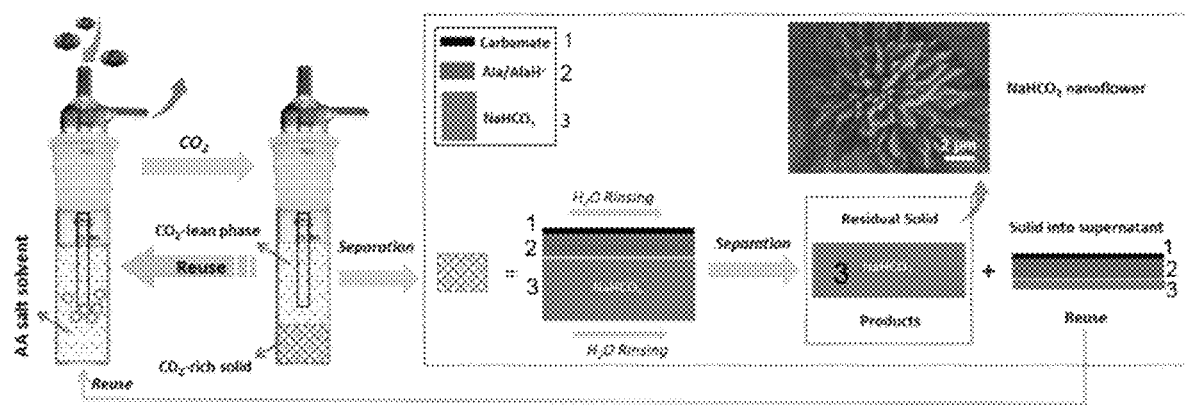
FIG. 6A is a schematic that shows the purification process of solid mixes to obtain $NaHCO_3$ solids of this invention. Ala-NaOH—$H_2O$ solution absorbs $CO_2$ and undergoes a self-concentrating process to form a $CO_2$-lean phase and a $CO_2$-rich phase with solid precipitates. The $CO_2$-rich phase undergoes a simple rinsing process, during which Ala and Ala carbamate solids dissolve in the rinsing water and are removed and reused; $NaHCO_3$ solids are left and may be used as a valuable product (e.g. baking soda).
Figure 6B:
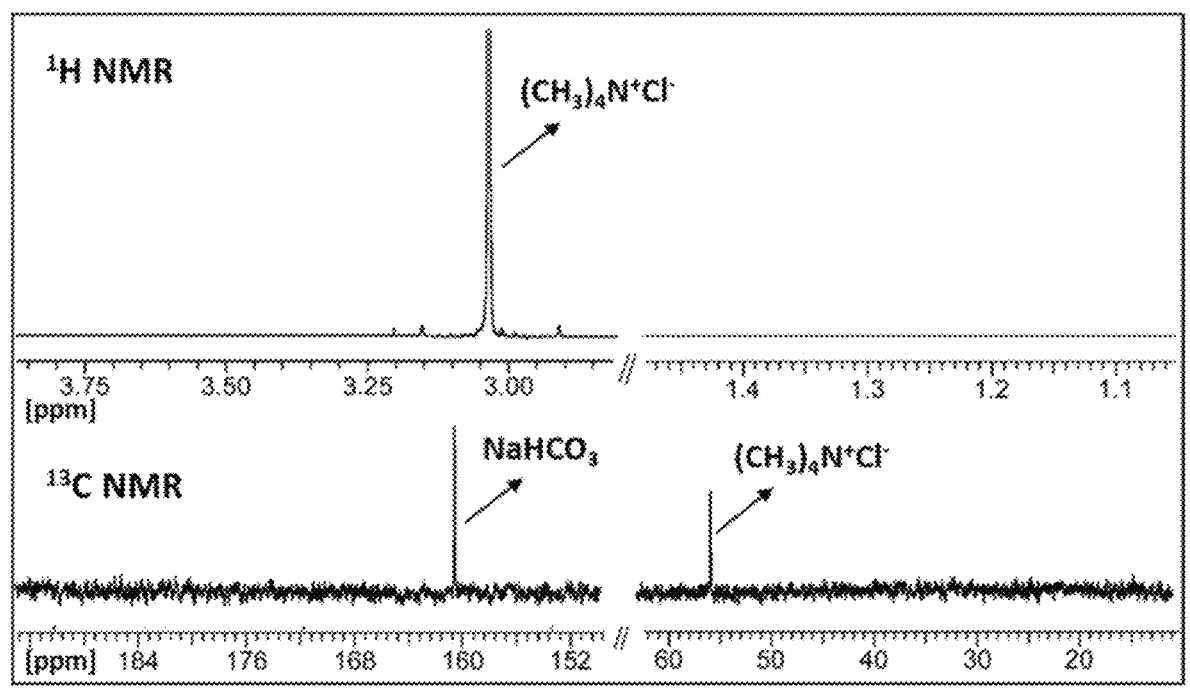
FIG. 6B shows the purification of solid mixes to obtain $NaHCO_3$ solids, $^1H$ NMR (upper) and C (lower) NMR spectra of remained solids after rinsing.
Figure 6C:
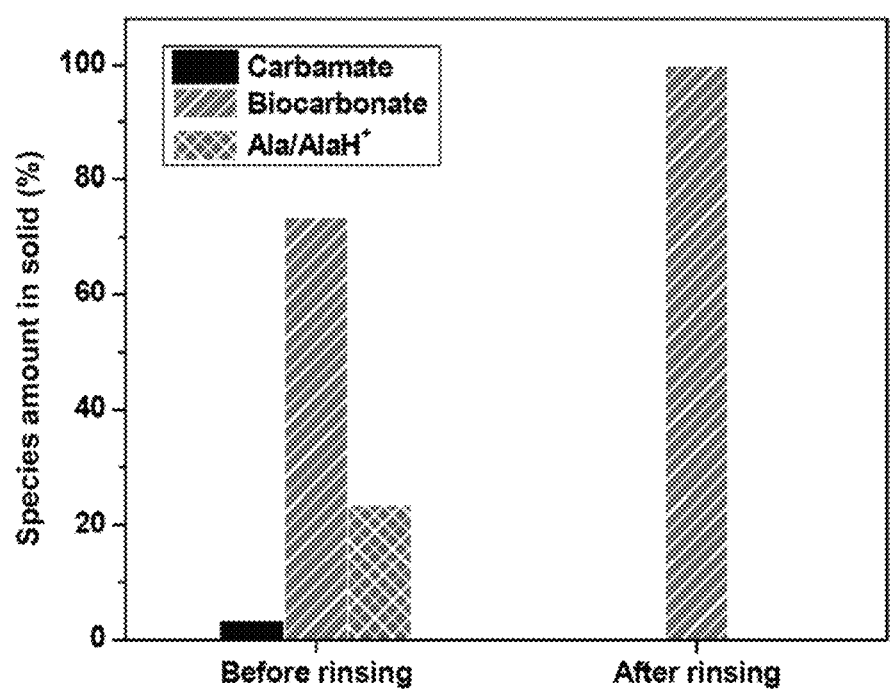
FIG. 6C shows the purification of solid mixes to obtain $NaHCO_3$ solids with species percentage in remaining solids before and after rinsing. The concentration of Ala in the Ala-NaOH—$H_2O$ solution was 17 wt % (weight percent) with a molar ratio of Ala:NaOH=1:2. In continuous stirred-tank reactor (CSTR) studies, Ala salt solution also converted $CO_2$ into $NaHCO_3$ nanoflowers and had high $CO_2$ absorption performance.

These unique properties of the self-concentrating amino acid solvents of the present invention, for example but not limited to the Ala-NaOH—$H_2O$ solution, offer the opportunity to obtain bicarbonate solids potentially as a commercially valuable chemical (e.g. baking soda). Since bicarbonate (73.5 wt %) was dominant in the solid mixes in the Ala-NaOH—$H_2O$ solution, a simple process was designed (FIG. 6A); $CO_2$ is absorbed in Ala-NaOH—$H_2O$ solution which self-concentrates and forms two distinct phases of $CO_2$-lean and $CO_2$-rich phases. The latter is separated from the $CO_2$-lean phase and undergoes a simple water rinsing step, during which solid Ala and its carbamate, and a small portion of bicarbonate dissolve and can be reused; Ala has a much higher solubility than $NaHCO_3$ in water at room temperature[43-45]. As a result, bicarbonate solid with a high purity can be achieved. Indeed, $NaHCO_3$, Ala/AlaH+, and Ala carbamate were present in the solid mixes before rinsing while, after rinsing with deionized water, only bicarbonate solids were obtained (FIGS. 6B and 6C) and more than 90% (ninety percent) of the bicarbonate solids was recovered. Note that bicarbonate solids could potentially be fully recovered if the solid mixes were rinsed with bicarbonate-saturated water. The significance of obtaining bicarbonate solids to serve as a potential commercial product include (i) offsetting the $CO_2$ capture costs by offering a commercially valuable product, (ii) eliminating the energy required for regeneration, (iii) reducing the concerns associated with the potential leakage of sequestered $CO_2$[46], and (iv) avoiding the transportation costs of conventional mineralization products to a sequestration site[22].

Figure 7A:
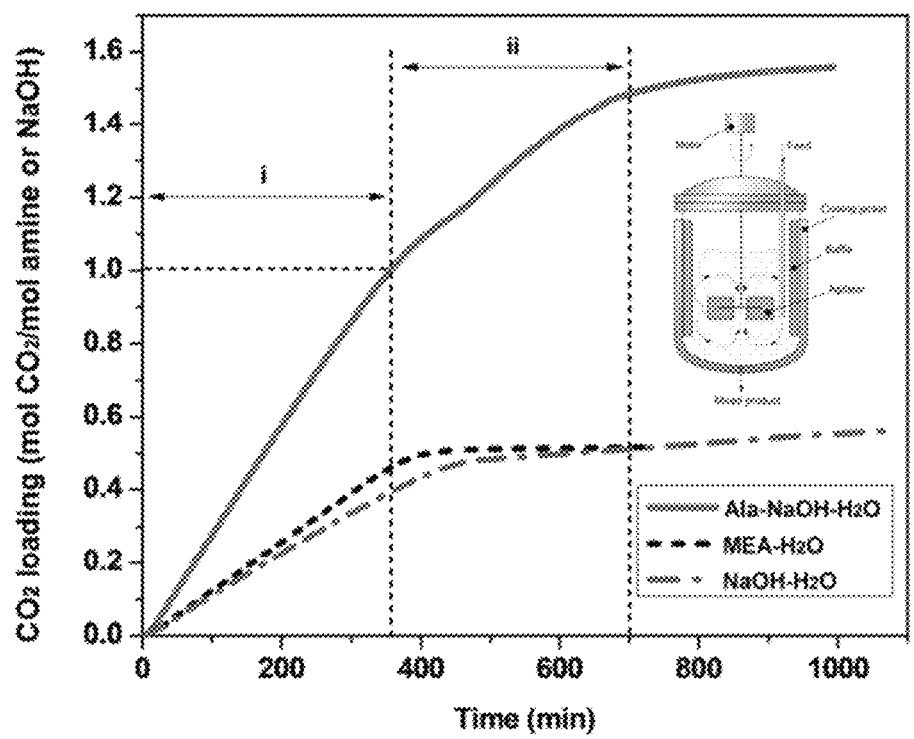
FIG. 7A shows the results of CSTR studies: $CO_2$ absorption performance of Ala-NaOH—$H_2O$ (i.e. the solvent of the present invention), MEA-$H_2O$, and NaOH—$H_2O$ control solutions. Inset shows the CSTR reactor schematic. To examine the potential for large scale studies, Ala-NaOH—$H_2O$ solution was also examined and compared with MEA-$H_2O$ and NaOH—$H_2O$ solutions under a simulated flue gas (10% $CO_2$ and 90% $N_2$) in CSTR. Monoethanolamine (MEA) is thought to be one of the most feasible processes for capturing a large amount of $CO_2$ that may be easily adopted by existing plants. [16]
Figure 7B:
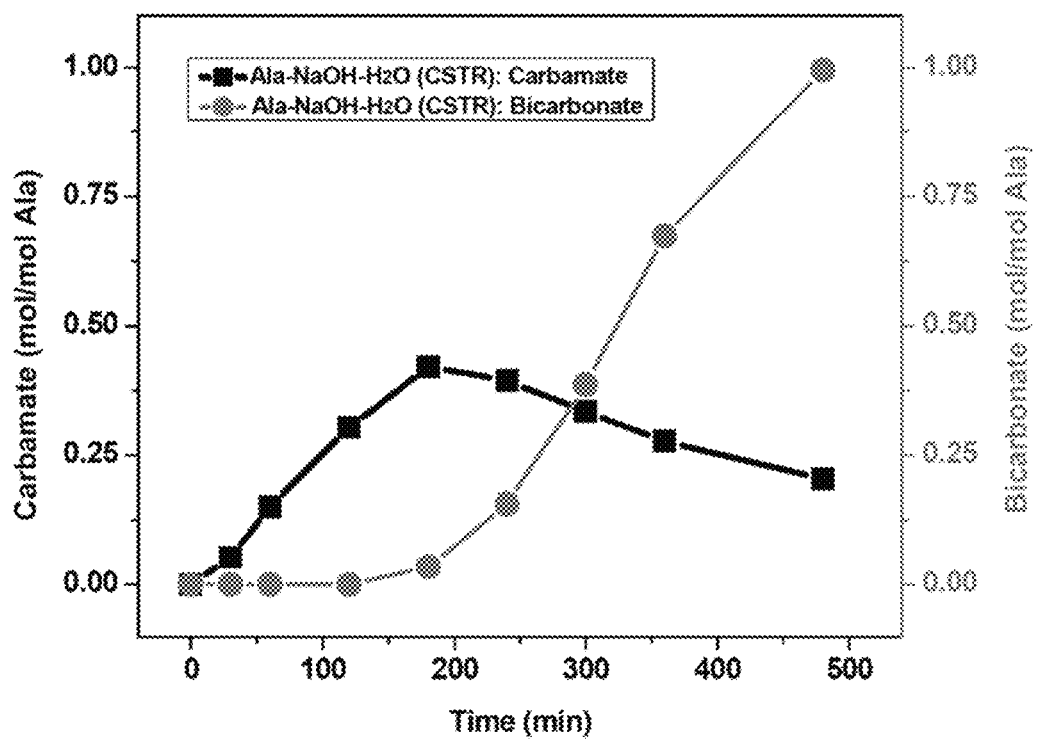
FIG. 7B shows the species changes as a function of $CO_2$ absorption time.

(3) In continuous stirred-tank reactor (CSTR) studies, Ala salt solution also converted $CO_2$ into $NaHCO_3$ nanoflowers and had high $CO_2$ absorption performance:

To examine the potential for large scale studies, Ala-NaOH—$H_2O$) solution was also examined and compared with MEA-$H_2O$ and NaOH—$H_2O$ solutions under a simulated flue gas (10% $CO_2$ and 90% $N_2$) in CSTR (FIGS. 7A and 7B). Monoethanolamine (MFA) is thought to be one of the most feasible processes for capturing a large amount of $CO_2$ that may be easily adopted by existing plants.[16]

Similar to the findings in 100% $CO_2$ and at small sample sizes, Ala-NaOH—$H_2O$ solution in the CSTR studies had distinct separation of two phases (i.e. a top clear phase and a bottom "milky" phase of $NaHCO_3$ nanoflowers and Ala particles). The Ala-NaOH—$H_2O$ solution also showed a clear two-stage $CO_2$ absorption: In the first absorption stage (I), the $CO_2$ absorption capacity increased linearly with increasing absorption time until about (~) 360 min. In the second absorption stage (II), the $CO_2$ absorption continued to increase almost linearly, although at a much slower rate compared to that of the first stage, until a capacity of ~(1.5 mol $CO_2$)/(mol Ala) was obtained at about (~) 700 min, after which there was not much change in $CO_2$ absorption (FIG. 7A). Ala carbamate was also found to form first in the Ala-NaOH—$H_2O$ solution, and the amount of Ala carbamate increased almost linearly with increasing $CO_2$ absorption time until 180 min, after which the amount of Ala carbamate decreased almost linearly with increasing $CO_2$ absorption time during 180-480 min (FIG. 7B). Meanwhile, no bicarbonate was detected until 180 min after which the amount of bicarbonate increased almost linearly with increasing $CO_2$ absorption time (FIG. 7B).

In the CSTR studies, the $CO_2$ absorption capacities of both MEA-$H_2O$ and NaOH—$H_2O$ control increased linearly with increasing $CO_2$ absorption time until 400 min, at which time their capacities were ~(0.50 mol $CO_2$)/(mol MEA) and (0.43 mol $CO_2$)/(mol NaOH), respectively (FIG. 7A). After 400 min, there was almost no change in the $CO_2$ absorption capacity in MEA-$H_2O$ solution and a very small but noticeable increase in NaOH—$H_2O$ solution (FIG. 7A). Compared to both MEA-$H_2O$ and NaOH—$H_2O$ solutions, Ala-NaOH—$H_2O$ solution had much faster absorption kinetics in its first absorption stage (I) (FIG. 7A).

TABLE 1

Species in Ala—NaOH—$H_2O$, MEA—$H_2O$ and NaOH—$H_2O$ control solutions after absorbing $CO_2$ for 700 min.

| Solvents | Carbamate | | Bicarbonate | | Carbonate | |
|---|---|---|---|---|---|---|
| | (mol/mol) | (%*) | (mol/mol) | (%*) | (mol/mol) | (%*) |
| MEA (30 wt %) | 0.35 | 94.6 | 0.02 | 5.4 | 0 | 0 |
| Ala—NaOH—$H_2O$ | 0.21 | 12.1 | 1.52 | 87.9 | 0 | 0 |
| NaOH control | 0 | 0 | 0.11 | 20.8 | 0.42 | 79.2 |

*Percentage among the species of carbamate, bicarbonate, and carbonate.

In addition, after reacting with $CO_2$, the MEA-$H_2O$ solution had a dominant MEA carbamate (94.6 wt % [weight percent]) with a very small portion of bicarbonate (5.4 wt %), the NaOH—$H_2O$ solution had mainly carbonate (79.2 wt %) together with a significant amount of bicarbonate (20.8 wt %), and the Ala-NaOH—$H_2O$ solution had dominant bicarbonate (87.9 wt %) with a small portion of Ala carbamate (12.1 wt %) and no carbonate at all (Table 1).

Figure 8:
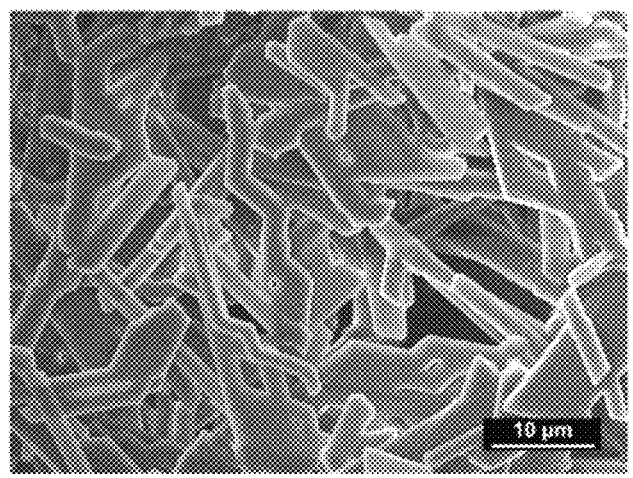
FIG. 8 is a FE-SEM image of solid precipitates formed in NaOH control solution.
Figure 9:
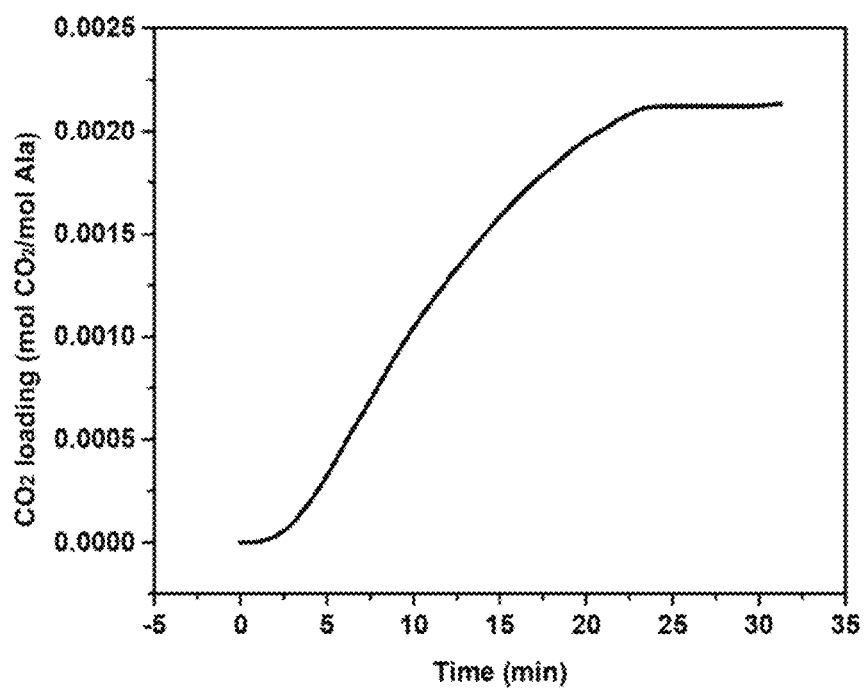
FIG. 9 shows the results of a CSTR study of $CO_2$ absorption performance of Ala-$H_2O$ solution (i.e. without NaOH).

Taken together, our studies showed that Ala played three key roles in $CO_2$ absorption in the Ala-NaOH—$H_2O$ system including (i) reacting with $CO_2$ to form Ala carbamate and bicarbonate resulting in high $CO_2$ absolution capacity, (ii) resulting in the formation of unique nanomaterials, and (iii) inhibiting the formation of carbonate from CO2 reacting with NaOH, based on the following evidence: (a) Ala carbamate formed first in the absorption process which subsequently hydrolyzed into bicarbonate, (b) no carbonate was ever observed in Ala-NaOH—$H_2O$ solutions while the NaOH—$H_2O$ control (without Ala) solution had carbonate dominance upon $CO_2$ absorption, and (c) under the same conditions, mainly large crystals of $NaHCO_3$ (FIG. 8) were observed in the NaOH—$H_2O$ control solutions. NaOH was also found to play an important role in the Ala-NaOH—$H_2O$ system by deprotonating protonated amino acids to enable Ala to react and absorb $CO_2$ based on the following evidence: Without NaOH, only negligible $CO_2$ absorption was detected in the Ala$H_2O$ solution (FIG. 9) while very high capacities [e.g. (1.55 mol $CO_2$)/(mol Ala) in the simulated flue gas] were obtained in Ala-NaOH—$H_2O$ solution.

Comparison to the-State-of-the-Art Technologies.

MEA and NaOH have been extensively studied for removing $CO_2$. For instance, Skyonic (San Antonio, Tex.) has recently developed a electrochemical production process to create NaOH to capture $CO_2$,[22,23] aiming to capture $CO_2$ in the region of 75,000 tons per year. Compared to NaOH scrubbing, the present method of this invention employing this inventions SCAA solvent produces unique $NaHCO_3$ nanomaterials and showed much higher $CO_2$ capacity with less material consumption (Table 2).[35] Compared to MEA, the SCAA solvent of the present invention undergoes a unique self-concentrating process and produces $NaHCO_3$ nanomaterials and has similar $CO_2$ capacity (based on weight) and material consumption. The regeneration of bicarbonate is energy-saving compared to the regeneration of carbamate. In addition, compared to MEA, amino acids have much lower volatility (due to their ionic nature), higher surface tension, and lower toxicity.

TABLE 2

Material consumption and species in solid part:
Comparison among Ala, NaOH, and MEA solutions.

| Solvents | $NaHCO_3$ | $CO_2$ loading in solid | Materials consumption[3] |
|---|---|---|---|
| AANaOH (30 wt %) | 13.94 g | 0.13 (g $CO_2$/g Solution) | AA: Fully recycle; NaOH: 0.17 (g/g solution)[1] |
| NaOH (20 wt %) | 2.34 g | 0.02 (g $CO_2$/g solution) | NaOH: 0.21 (g/g solution) |
| MEA[2] (30 wt %) | — | 0.11 (g $CO_2$/g solution) (No solid) | MEA[2] (0.15 g/g solution) |

[1]AA fully recycle was based or the reaction and rising procedure; NaOH consumption in 1 cycle was calculated based on reaction
[2]MEA: $CO_2$ loading is less than alanine system [0.11 (g $CO_2$/g solution)]
[3]NaOH is much cheaper than MEA A Process to Capture $CO_2$ while Producing Amino Acid Nanofibers.

Figure 10:
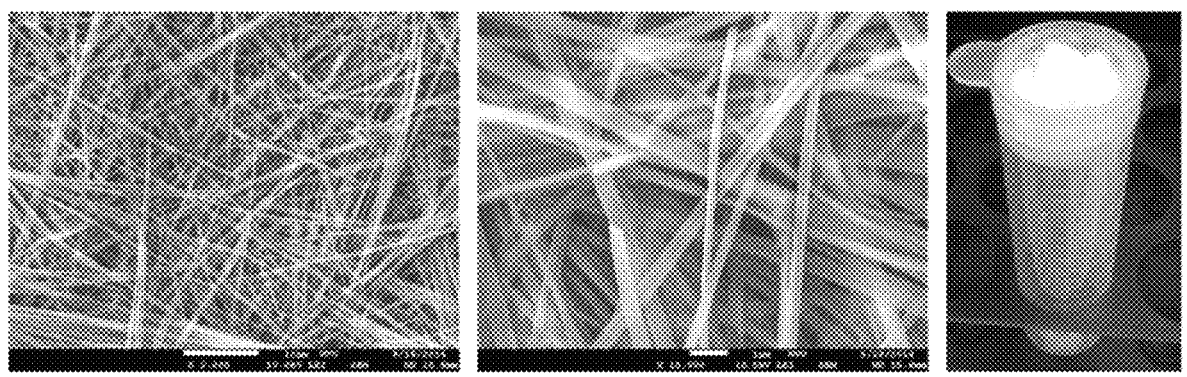
FIG. 10 shows the morphology of amino acid nanofibers (i.e, phenylalanine nanofibers) formed during $CO_2$ bubbling into Phe-NaOH—$H_2O$ solution.
Figure 11:
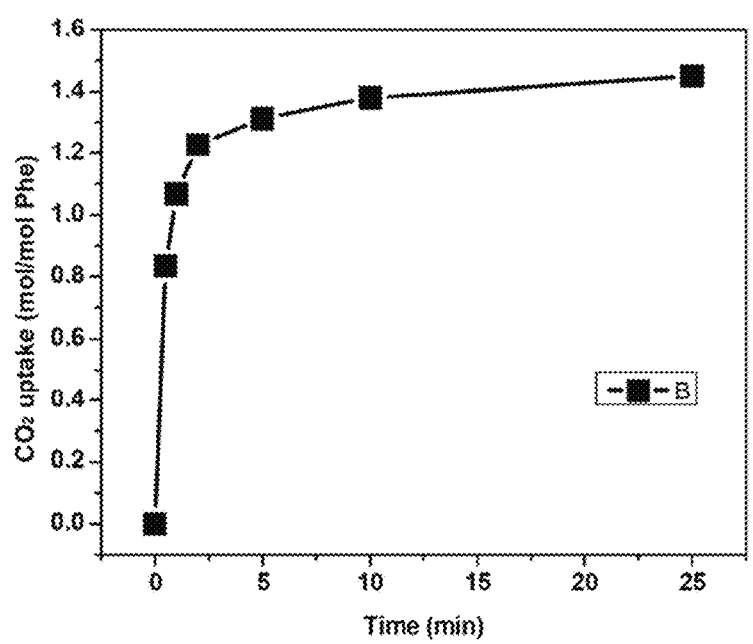
FIG. 11 shows $CO_2$ uptake in Phe-NaOH—$H_2O$ solution. Phe-0.2M-NaOH—$CO_2$-precipitate ($H_2O$ washed).
Figure 12:
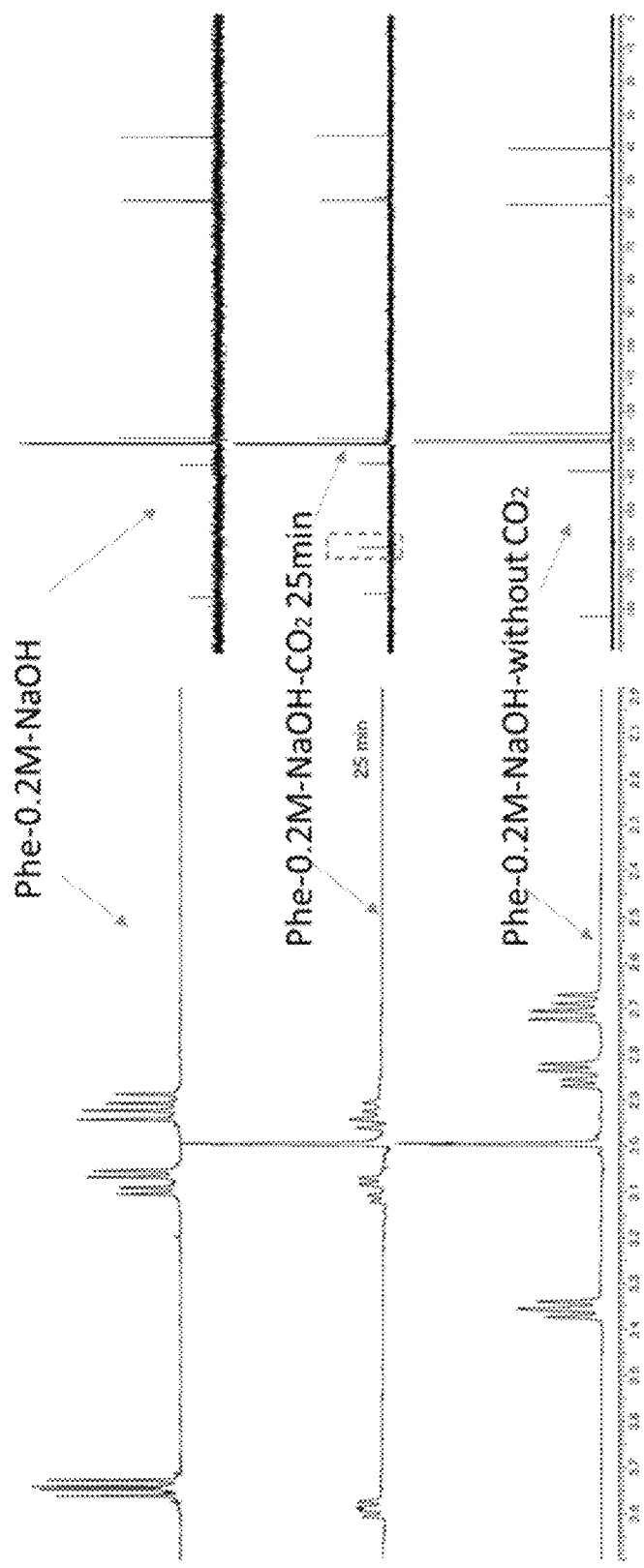
FIG. 12 shows NMR data of the nanofibers formed during $CO_2$ bubbling into Phe-NaOH—$H_2O$ solution of this invention.

The aforementioned is about the production of unique $NaHCO_3$ nanofibers and nanoflowers. Besides $NaHCO_3$ nanomaterials, we also developed a process to fabricate amino acid nanofibers during $CO_2$ absorption. By tuning the Phe-NaOH—$H_2O$ system, we produced large quantities of Phe nanofibers (FIG. 10) and achieved a significant $CO_2$ capture capacity (FIG. 11). NMR tests (FIG. 12) confirmed that the nanofibers were Phe (not $NaHCO_3$) and $CO_2$ was absorbed as $NaHCO_3$.

Those persons skilled in the art will understand that the present invention provides methods for innovative $CO_2$ capture and utilization including (i) turning $CO_2$ into $NaHCO_3$ nanofibers and nanoflowers, and provides (ii) self-concentrating $NaHCO_3$ nanomaterials for easy separation and reuse, and discloses (iii) methods that lead to both $CO_2$ absorption and amino acid nanofiber formation.

EXAMPLES OF USES OF THE DISCLOSED INVENTION

Market for Bicarbonate Nanomaterials:

(i) As new nanomaterials, sharing the nanomaterials market (>$11 billion a year with an impact of over $340 billion):

(ii) As temporary supports for drug encapsulation, which has a yearly market of billions of dollars. According to a recent report from Transparency Market Research, the micro- and nano-encapsulation market has a worldwide market of $4.77 billion in 2013 and was projected to increase to $9.13 billion in 2020. North America and Europe together held 70% of the global encapsulation market. More than 65% of the micro- and nano-encapsulation market in 2013 was for pharmaceuticals in which the encapsulation allows for targeted drug delivery and release, sustained and controlled release of active ingredients, and masking of chemicals odors.

(iii) As a therapeutic drug, with improved efficacy due to its nano-size, to treat a variety of medical issues including, for example but not limited to, heartburn, indigestion, high acid levels in blood or urine, relief of insect-bite symptoms etc. It has a significant market:

| Disease/Symptom | Prevalence and Occurrence | Medical and Other Costs |
|---|---|---|
| Gastroesophageal reflux disease (GERD), heart burn, or acid reflux | ~7 million people in the U.S. have some symptoms of GERD. 60% of the adult population will experience some type of GERD within a 12 month period and 2030% will have weekly symptoms. | ~3.1 million people were hospitalized in the U.S. in 2004 for GERD-related symptoms, complications, and treatment. There are ~64.6 million prescriptions written for GERD medications in the U.S. on an annual basis. It's estimated by the American College of Gastroenterology that the symptoms of GERD result in almost $2 billion in lost productivity each week of the year. |

| Disease/Symptom | Prevalence and Occurrence | Medical and Other Costs |
|---|---|---|
| Dyspepsia (indigestion) | Prevalance Rate: ~3.5% or 9.5 million people in U.S. Incidence: 6 million cases annually in U.S. | 98% of hospital consultant episodes for dyspepsia required hospital admission in England 2002-03; data of U.S. not found. |

(iv) As nano-baking soda, having a market of 42 million tons in 2005.
(v) To be used at the incinerator for flue gasses cleaning purposes (removal of acid components), thus avoiding the current expensive purchase of sodium bicarbonate.

In addition, due to the easy removal (e.g. via heating at 50 degrees C. (Centigrade) or mild acid washing), bicarbonate nanomaterials may be used as templates to make unique hollow micro-nano-structured materials that can play an important role in cutting edge innovations for energy conversion and storage technologies such as for example but not limited to solar cells, fuel cells, lithium ion batteries and super capacitors [Energy Environ. Sci., 2012, 5, 5604-/8].

Market for Amino Acid Nanofibers:
(i) Tissue engineering: amino acid nanofibers can be used as scaffolds for musculoskeletal tissue engineering (including bone, cartilage, ligament, and skeletal muscle), skin tissue engineering, vascular tissue engineering, neural tissue engineering, and as carriers for the controlled delivery of drugs, proteins, and DNA. The U.S. market for tissue engineering products for musculoskeletal applications (as an example) is $18 billion in 2010, and the total potential market for these products is expected to exceed $39 billion in the year 2019.
(ii) Biomaterials such as wound dressing, hydrogels etc. The global wound care market is expected to reach $18.3 billion by 2019 from $15.6 billion in 2014.
(iii) Filtration and catalyst supports, etc. As an example, application of filtration technologies in pharmaceutical and biotechnological as well as food and beverage laboratories has a market of $1,805 million in 2014 and is expected to grow at 7% from 2014 to 2019.

This invention will lead to the following uses:

This invention sets forth $CO_2$ capture technologies that not only will effectively and efficiently capture $CO_2$ but also will simultaneously convert $CO_2$ emission into unique nanomaterials and commercially valuable chemicals or produce amino acid nanofibers. Uses may include for example but not limited to:
  Capture $CO_2$ from power plants, air, etc.;
  Capture and convert $CO_2$ into commercial products including nanomaterials. No catalysts are required for the $CO_2$ conversion;
  Fabricate large quantities of unique nanomaterials including organic and inorganic nanofibers, nanowires, and nanoparticles;
  Produce baking soda or amino acid nanomaterials in large quantities;
  Capture $CO_2$ from air and enclosed environment such as space station or space ship, submarine etc.;
  Capture other greenhouse gases; and
  Purify water etc. based on, for example, self-concentrating and formation of precipitates.

The technology will be of great interest to power plants and natural gas companies and other resources that generate greenhouse gases (for $CO_2$ capture and utilization), and to companies that are interested in or selling new products and producing large quantities of $NaHCO_3$ nanomaterials and amino acid nanofibers.

Products would include for example but not limited to: Technology to convert $CO_2$, into products without the use of catalysts, technology to produce amino acid nanofibers during $CO_2$ absorption, commercial products for daily life or research uses such as baking soda, amino acid nanofibers, and $NaHCO_3$ nanomaterials.

REFERENCES

[1] Yang S, Lin X, Lewis W, Suyetin M, Bichoutskaia E, Parker J E, et al. A partially interpenetrated metal-organic framework for selective hysteretic sorption of carbon dioxide. Nature materials. 2012; 11:710-6.
[2] Yue M, Hoshino Y, Ohshiro Y, Imamura K, Miura Y. Temperature-Responsive Microgel Films as Reversible Carbon Dioxide Absorbents in Wet Environment. Angew Chem-Ger Edit. 2014; 126:2692-5.
[3] Pacala S, Socolow R. Stabilization wedges: Solving the climate problem for the next 50 years with current technologies. Science. 2004; 305:968-72,
[4] Lin L C, Berger A H, Martin R L, Kim J, Swisher J A, Jariwala K, et al. In silico screening of carbon-capture materials. Nat Mater. 2012; 11:633-41.
[5] Mauna Loa Observatory. Hawaii http://co2now.orti/ (2014).
[6] Tollefson J. Growing agricultural benefits for climate. Nature. 2009; 462:966-.
[7] 2030 framework for climate and energy policies. http://eceuropaeu/clima/policies/2n3Q/index enhtm. 2014.
[8] Chu S. Carbon Capture and Sequestration. Science. 2009; 325:1599.
[9] Gao W-Y, Chen Y, Niu Y, Williams K, Cash L, Perez P J, et al. Crystal Engineering of an nbo Topology Metal-Organic Framework for Chemical Fixation of CO2 under Ambient Conditions. Angewandte Chemie International Edition. 2014; 53:2615-9.
[10] Mathieu P. The IPCC special report on carbon dioxide capture and storage. ECOS 2006: Proceedings of the 19th International Conference on Efficiency, Cost, Optimization, Simulation and Environmental Impact of Energy Systems, Vols 1-3. 2006:1611-7.
[11] Massood R Timothy, J. S., Nsakala ya, N. & Liljedahl, G. N. Carbon Dioxide Capture from Existing Coal-Fired Power Plants (National Energy Technology Laboratory, US Department of Energy, 2007).
[12] D'Alessandro D M, Smit B, Long J R. Carbon Dioxide Capture: Prospects for New Materials. Angew Chem int Edit. 2010; 49:6058-82.
[13] Yong Z, Mata V G, Rodrigues A E. Adsorption of carbon dioxide on chemically modified high surface area carbon-based adsorbents at high temperature. Adsorption. 2001; 7:41-50.
[14] Li B Y, Duan Y H, Luebke D, Morreale B. Advances in CO2 capture technology: A patent review. Appl Energ. 2013; 102:1439-47.
[15] MacDowell N, Florin N, Buchard A, Hallett J, Galindo A, Jackson G, et al. An overview of CO2 capture technologies. Energy & Environmental Science. 2010; 3:1645.
[16] Anderson S, Newell R. Prospects for carbon capture and storage technologies. Annu Rev Env Resour. 2004; 29:109-42.

[17] Haszeldine R S. Carbon Capture and Storage: How Green Can Black Be? Science, 2009; 325:1647-52.
[18] Little M G, Jackson R B. Potential Impacts of Leakage from Deep CO2 Geosequestration on Overlying Freshwater Aquifers. Environ Sci Technol. 2010; 44:9225-32.
[19] Kim S H, Kim K R Hong S H, Carbon Dioxide Capture and Use: Organic Synthesis Using Carbon Dioxide from Exhaust Gas. Angew Chem Int Edit. 2014; 53:771-4.
[20] Moret S, Dyson P J, Laurenczy G. Direct synthesis of formic acid from carbon dioxide by hydrogenation in acidic media. Nat Commun. 2014; 5.
[21] Behrens M, Studt F, Kasatkin I, Kuhl S, Havecker M, Abild-Pedersen F, et al. The Active Site of Methanol Synthesis over Cu/ZnO/Al2O3 Industrial Catalysts. Science. 2012; 336:893-7.
[22] Damiani D, Litynski J T, McIlvried H G, Vikara D M, Srivastava R D. The US department of Energy's R&D program to reduce greenhouse gas emissions through beneficial uses of carbon dioxide. Greenhouse Gases: Science and Technology. 2012; 2:9-16.
[23] Jones J D. Removing carbon dioxide from waste streams through co-generation of carbonate and/or bicarbonate minerals. U.S. Pat. No. 7,727,374; 2010.
[24] Gebreeyessus G D, Kaba T, Chandravanshi B S. Removing carbon dioxide from a stationary source through co-generation of carbonate/bicarbonate: The case of Mugher cement factory. African Journal of Environmental Science and Technology. 2014; 8:75-85.
[25] Stauffer P H, Keating G N, Middleton R S, Viswanathan H S, Berchtod K A, Singh R P, et al. Greening Coal: Breakthroughs and Challenges in Carbon Capture and Storage. Environmental science & technology. 2011; 45:8597-604.
[26] Jiang B, Wang X, Gray M L, Duan Y, Luebke D, Li B. Development of amino acid and amino acid-complex based solid sorbents for CO2 capture. Applied Energy. 2013; 109:112-8.
[27] Wang X, Akhmedov N G, Duan Y, Luebke D, Li B. Immobilization of amino acid ionic liquids into nanoporous microspheres as robust sorbents for CO2 capture. Journal of Materials Chemistry A. 2013; 1:2978-82.
[28] Wang X, Akhmedov N G, Duan Y, Luebke D, Hopkinson D, Li B. Amino acid-fimctionalized ionic liquid solid sorbents for post-combustion carbon capture. ACS applied materials & interfaces. 2013; 5:8670-7.
[29] Muñoz D M, Portugal A F, Lozano A E, Jose G, de Abajo J. New liquid absorbents for the removal of CO2 from gas mixtures. Energy Environ Sci. 2009; 2:883-91.
[30] Jiang B B, DeFuseo E, Li B Y. Polypeptide Multilayer Film Co-Delivers Oppositely-Charged Drug Molecules in Sustained Manners. Biomacromolecules. 2010; 11:3630-7.
[31] Li B Y, Jiang B B, Boyce B M, Lindsey B A. Multilayer polypeptide nanoscale coatings incorporating IL-12 for the prevention of biomedical device-associated infections. Biomaterials, 2009; 30:2552-8.
[32] Jiang B B, Li B Y. Tunable drug loading and release from polypeptide multilayer nanofilms. International journal of nanomedicine. 2009; 4:37-53.
[33] Jiang B B, Li B Y. Polypeptide Nanocoatings for Preventing Dental and Orthopaedic Device-Associated Infection: pH-Induced Antibiotic Capture, Release, and Antibiotic Efficacy. J Biomed. Mater Res B. 2009; 88B: 332-8.
[34] Jiang B, Barnett J B, Li B. Advances in polyelectrolyte multilayer nanofillms as tunable drug delivery systems. Nanotechnology, science and applications. 2009; 2:21.
[35] Knuutila H, Aronu U E, Kvamsdal H M, Chikukwa. A. Post combustion CO2 capture with an amino acid salt. Energy Procedia. 2011; 4:1550-7.
[36] Portugal A F, Sousa J M, Magalhaes F D, Mendes A. Solubility of carbon dioxide in aqueous solutions of amino acid salts. Chemical Engineering Science. 2009; 64:1993-2002.
[37] Majchrowicz M E, Brilman D W F, Groeneveld M J, Precipitation regime for selected amino acid salts for CO2 capture from flue gases. Energy Procedia. 2009; 1:979-84.
[38] Song H-J, Park S, Kim H, Gaur A, Park J-W, Lee S-J. Carbon dioxide absorption characteristics of aqueous amino acid salt solutions. International Journal of Greenhouse Gas Control. 2012; 11:64-72.
[39] Kumar P S, Hogendoom J A, Feron P H M, Versteeg G F. Equilibrium solubility of CO2 in aqueous potassium taurate solutions: Part 1. Crystallization in carbon dioxide loaded aqueous salt solutions of amino acids. Industrial & engineering chemistry research. 2003; 42:2832-40.
[40] Sanchez-Fernandez E, Mercader FdM, Misiak K, van der Ham L, Linders M, Goetheer E. New Process Concepts for CO2 Capture based on Precipitating Amino Acids. Energy Procedia. 2013; 37:1160-71.
[41] Hook R J. An investigation of some sterically hindered amines as potential carbon dioxide scrubbing compounds. Industrial & engineering chemistry research. 1997; 36:1779-90.
[42] Kumar P S, Hogendoom J A, Timmer S J, Feron P H M, Versteeg G F. Equilibrium solubility of CO2 in aqueous potassium taurate solutions: Part 2. Experimental V L E data and model. Industrial & engineering chemistry research. 2003; 42:2841-52.
[43] Tseng H C, Lee C Y, Weng W L, Shiah I M. Solubilities of amino acids in water at various pH values under 298.15 K. Fluid Phase Equilibria. 2009; 285:90-5.
[44] Dunn M S, Ross F J, Read L S. The solubility of the amino acids in water. Journal of Biological Chemistry. 1933; 103:579-95.
[45] Needham T E, Paruta A, Gerraughty R. Solubility of amino acids in pure solvent systems. J Pharm Sci. 1971; 60:565-7.
[46] Bhaduri G A, Sitter L. Nickel nanoparticles catalyse reversible hydration of carbon dioxide for mineralization carbon capture and storage. Catal Sci Technol. 2013; 3:1234-9.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A method for converting carbon dioxide into NaHCO$_3$ nanofibers or nanoflowers consisting of subjecting a source of carbon dioxide to an amino acid containing aqueous salt solution consisting of an amino acid that is alanine, a base solvent that is either NaOH or KOH, and water without the use of a catalyst for producing a CO$_2$ lean phase of an alanine-NaOH or KOH solution and a CO$_2$ rich phase that is a NaHCO$_3$ nanomaterial precipitate.

2. The method of claim 1 including wherein said amino acid containing aqueous salt solution is Ala-NaOH—H$_2$O.

3. The method of claim 1 wherein said CO$_2$ rich phase is a NaHCO$_3$ solid product.

4. The method of claim 3 wherein said NaHCO$_3$ solid product is subject to a purification process to form a purified bicarbonate solid product.

5. The method of claim 4 including wherein said purified bicarbonate solid product is subjected to heat for achieving an increased concentration of a carbon dioxide gas.

* * * * *